(12) United States Patent
Nelson et al.

(10) Patent No.: US 8,062,654 B2
(45) Date of Patent: Nov. 22, 2011

(54) DRUG RELEASING BIODEGRADABLE FIBER FOR DELIVERY OF THERAPEUTICS

(75) Inventors: Kevin D. Nelson, Arlington, TX (US); Brent B. Crow, Fort Worth, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 1295 days.

(21) Appl. No.: 11/347,474

(22) Filed: Feb. 3, 2006

(65) Prior Publication Data

US 2006/0193769 A1    Aug. 31, 2006

Related U.S. Application Data

(63) Continuation of application No. 10/428,901, filed on May 2, 2003, now Pat. No. 7,033,603, which is a continuation-in-part of application No. 09/632,457, filed on Aug. 4, 2000, now Pat. No. 6,596,296.

(60) Provisional application No. 60/147,827, filed on Aug. 6, 1999.

(51) Int. Cl.
*A61F 2/02* (2006.01)

(52) U.S. Cl. ........................................ 424/426

(58) Field of Classification Search .................. None
See application file for complete search history.

(56) References Cited

U.S. PATENT DOCUMENTS

| | | | |
|---|---|---|---|
| 4,464,321 A | 8/1984 | Pittalis et al. | 264/83 |
| 4,965,128 A | 10/1990 | Greidanus et al. | 428/398 |
| 5,166,187 A | 11/1992 | Collombel et al. | 514/21 |
| 5,263,984 A | 11/1993 | Li et al. | 623/15 |
| 5,270,300 A | 12/1993 | Hunziker | 514/12 |
| 5,290,271 A | 3/1994 | Jernberg | 604/891.1 |
| 5,342,348 A | 8/1994 | Kaplan | 605/891.1 |
| 5,567,612 A | 10/1996 | Vacanti et al. | 435/240.23 |

FOREIGN PATENT DOCUMENTS

| | | |
|---|---|---|
| EP | 0 328 050 A2 | 8/1989 |
| EP | 0454599 A1 | 10/1991 |
| JP | 06-296673 A | 10/1994 |
| JP | 09-078456 A | 3/1997 |
| JP | 09-176969 A | 7/1997 |
| JP | 10-212456 A | 8/1998 |
| WO | WO 98/20190 | 5/1998 |
| WO | WO 00/47716 | 8/2000 |
| WO | WO-01/10421 A1 | 2/2001 |
| WO | WO-0218441 A2 | 3/2002 |
| WO | WO-03/087444 A1 | 10/2003 |

OTHER PUBLICATIONS

Lopez Garcia, Monica, "Supplementary European Search Report", as completed Jan. 20, 2010 (6 pages).

(Continued)

*Primary Examiner* — Carlos Azpuru
(74) *Attorney, Agent, or Firm* — Winstead PC

(57) ABSTRACT

The present invention relates to fiber compositions comprising gels or hydrogels. The invention further relates to the composition of a gel or hydrogel loaded biodegradable fiber and methods of fabricating such fibers. The present invention further provides tissue engineering and drug-delivery compositions and methods wherein three-dimensional matrices for growing cells are prepared for in vitro and in vivo use. The invention also relates to methods of manipulating the rate of therapeutic agent release by changing both the biodegradable polymer properties as well as altering the properties of the incorporated gel or hydrogel.

11 Claims, 11 Drawing Sheets

OTHER PUBLICATIONS

Aigner et al., "Cartilage tissue engineering with novel nonwoven structured biomaterial based on hyaluronic acid benzyl ester," *J. of Biomed. Materials Res.*, 42(2):172-81, 1998.

Auerbach and Auerbach, "Angiogenesis inhibition: a review," *Pharmac. Ther.*, 63:265, 1994.

Breitbart et al., "Tissue engineered bone repair of calvarial defects using cultured periosteal cells," *Plastic & Reconstructive Surgery*, 101(3):567-74, 1998.

Cao et al., "Comparative study of the use of poly(glycolic acid), calcium alginate and pluronics in the engineering of autologous porcine cartilage," *J. of Biomaterials Sci., Polymer Edition*, 9(5):475-87, 1998.

Dillon et al., "The influence of physical structure and charge on neurite extension in a 3D hydrogel scaffold," *J. of Biomaterials Sci., Polymer Ed.*, 9(10):1049-69, 1998.

Elcin et al., "Xenotransplantation of fetal porcine hepatocytes in rats using a tissue engineering approach," *Artificial Organs*, 23(2):146-52, 1999.

Fidler and Ellis, "The implications of angiogenesis for the biology and therapy of cancer metastasis," *Cell*, 79:185, 1994.

Folkman and Klagsbrun, "Angiogenic factors," *Science*, 235:442-447, 1987.

Folkman, "How is blood vessel growth regulated in normal and neoplastic tissue," *Cancer Res.*, 46:467, 1986.

Folkman, J., "Angiogenesis in cancer, vascular, rheumatoid and other disease," *Nature Med.*, 1:27, 1995.

Grande et al., "Evaluation of matrix scaffolds for tissue engineering of articular cartilage grafts," *J. of Biomed. Mat. Res.*, 34(2):211-20, 1997.

Gutsche et al., "Engineering of a sugar-derivatized porous network for hepatocyte culture," *Biomaterials*, 17(3):387-93, 1996.

Hoerstrup et al., "Tissue engineering: a new approach in cardiovascular surgery-seeding of human fibroblasts on resorbable mesh," *Swiss Surgery*, (Suppl.), 2:23-5, 1998.

Hoerstrup et al., "Fluorescence activated cell sorting: a reliable method in tissue engineering of a bioprosthetic heart valve," *Annals of Thoracic Surgery*, 665(5):1653-7, 1998.

Isogai et al., "Formation of phalanges and small joints by tissue-engineering," *J. of Bone & Joint Surgery, American* vol. 81(3):306-16, 1999.

Martin et al., "In vitro differentiation of chick embryo bone marrow stromal cells into cartilaginous and bone-like tissues," *J. of Orthopaedic Res.*, 16(2):181-9, 1998.

Nagy et al., "Pathogenesis of ascites tumor growth: vascular permeability factor, vascular hyperpermeability, and ascites fluid accumulation," *Cancer Res.*, 55:360, 1995.

Peppas and Langer, "New challenges in biomaterials," *Science*, 263:1715-1720, 1994.

Peter et al., "Polymer concepts in tissue engineering," *J. of Biomed. Materials Res.*, 43(4):422-7, 1998.

Sacks et al., "Collagen fiber architecture of a cultured dermal tissue," *J. of Biomed. Engineering*, 119(1):124-7, 1997.

Shinoka et al., "Creation of viable pulmonary artery autografts through tissue engineering," *J. of Thoracic & Cardiovascular Surgery*, 115(3):536-45, 1998.

Sims et al., "Tissue engineered neocartilage using plasma derived polymer substrates and chondrocytes," *Plastic & Reconstructive Surgery*, 101(6):1580-5, 1998.

Vunjak-Novakovic et al., "Dynamic cell seeding of polymer scaffolds for cartilage tissue engineering," *Biotechnology Progress*, 14(2):193-202, 1998.

Whang et al., "Ectopic bone formation via rhBMP-2 delivery from porous bioabsorbably polymer scaffolds," *J. of Biomed. Materials Res.*, 42(4):491-9, 1998.

Wong and Mooney, "Synthesis and properties of biodegradable polymers used in tissue engineering," *In: Synthetic Biodegradable Polymer Scaffolds*, (Atala and Mooney, eds.), Birkhauser Press, Boston, MA, pp. 51-82, 1997.

Yoo and Atala, "A novel gene delivery system using urothelial tissue engineered neoorgans," *J. of Urology*, 158(3 Pt 2):1066-70, 1997.

Fauza et al., "Videofetoscopically assisted fetal tissue engineering: skin replacement," *J. of Pediatric Surgery*, 33(2):357-61, 1998.

DRUG RELEASING BIODEGRADABLE FIBER FOR DELIVERY OF THERAPEUTICS

CROSS REFERENCES TO RELATED APPLICATIONS

This application is a continuation of application Ser. No. 10/428,901, filed May 2, 2003, now U.S. Pat. No. 7,033,603, which is a continuation-in-part of application Ser. No. 09/632,457, filed Aug. 4, 2000, U.S. Pat. No. 6,596,296, which claims the benefit of U.S. Provisional Application No. 60/147,827, filed Aug. 6, 1999.

BACKGROUND OF THE INVENTION

1. Field of the Invention

This invention relates to the field of medicine and tissue engineering, and in particular to drug releasing biodegradable fibers used in the delivery of therapeutics.

2. Description of Related Art

Tissue engineering is a discipline wherein living cells are used to replace cells lost as a result of injury, disease, or birth defect in an animal or human. These replacement cells can be autologous, allogenic, or xenogenic. The field of tissue engineering is a new area of medicine and optimal procedures have yet to be elucidated.

At present, there are several avenues for engineering tissues. One avenue is to harvest cells from a healthy donor, preferably from the same individual, or at least from an appropriate donor of the same species, and grow those cells on a scaffold in vitro. This scaffold is typically a three-dimensional polymer network, often composed of biodegradable fibers. Cells adherent to the polymer network can then typically be induced to multiply. This cell filled scaffold can be implanted into the impaired host with the goal that the cells will perform their physiological function and avoid destruction by the host immune system. To this end, it is important that purified cell lines are used, as the introduction of non-self immune cells can up-regulate a strong host immune attack. The difficulty with this approach is the scaffolding must be small, as no cell can survive more than a couple millimeters away from a source of oxygen and nutrients. Therefore, large scaffolds cannot be used, as the scaffold will not vascularize adequately in time to save the cells in the interior regions.

In another approach, an empty three-dimensional, biodegradable polymer scaffold is directly implanted in the patient, with the goal of inducing the correct type of cells from the host's body to migrate into the polymer scaffold. The benefit is that vascularization can happen simultaneously with migration of cells into the matrix. A major problem is that there is currently no way to ensure that the appropriate cell types will migrate into the scaffold, and that the mechanical and biological properties will be maintained to provide the patient's physiological need.

In both of the above approaches, the scaffold may be biodegradable, meaning that over time it will break down both chemically and mechanically. As this break down occurs, the cells secrete their own extracellular matrix, which plays a critical role in cell survival and function. In normal tissue, there is an active and dynamic reciprocal exchange between the constitutive cells of the tissue and the surrounding extracellular matrix. The extracellular matrix provides chemical signals that regulate the morphological properties and phenotypic traits of cells and may induce division, differentiation or even cell death. In addition, the cells are also constantly rearranging the extracellular matrix. Cells both degrade and rebuild the extracellular matrix and secrete chemicals into the matrix to be used later by themselves or other cells that may migrate into the area. It has also been discovered that the extracellular matrix is one of the most important components in embryological development. Pioneering cells secrete chemical signals that help following cells differentiate into the appropriate final phenotype. For example, such chemical signals cause the differentiation of neural crest cells into axons, smooth muscle cells or neurons.

The integrated relationship between extracellular matrix and tissue cells establishes the extracellular matrix as an important parameter in tissue engineering. If cells are desired to behave in a specific manner, then the extracellular matrix must provide the appropriate environment and appropriate chemical/biological signals to induce that behavior for that cell type. Currently it is not possible to faithfully reproduce a biologically active extracellular matrix. Consequently, some investigators use a biodegradable matrix that enables the cells to create their own extracellular matrix as the exogenous matrix degrades.

In the above-described approaches to tissue engineering, a polymer scaffold provides not only the mechanical support, but also the three-dimensional shape that is desired for the new tissue or organ. Because cells must be close to a source of oxygen and nutrients in order to survive and function, a major current limitation is that of blood supply. Most current methodologies provide no specific means of actively assisting the incorporation of blood vessels into and throughout the polymer matrix. This places limitations on the physical size and shape of the polymer matrix. The only current tissue engineering device that has made it into widespread clinical use is artificial skin, which by definition is of limited thickness. The present invention provides compositions and methods that promote the directed migration of appropriate cell types into the engineered extracellular matrix. By directing specific three-dimensional cell migration and functional patterns, directed vascularization can be induced, which overcomes the current limitations on the shape and size of polymer implants. It also ensures that appropriate cell types will be physically located in specific locations within the matrix. Compositions and methods are provided to modulate phenotypic expression as a function of both time and space.

Most of the drug delivery from polymeric drug-loaded vehicles is based on the following formats: microspheres, nano-particles, foams, films, liposomes, polymeric micelles, or viral packages. There are a number of inherent disadvantages with respect to the above mentioned formats. Several of the above mentioned drug delivery formats do not remain in place after they have been implanted. As a result retrieval of the implant is not possible in the case of an adverse reaction to the implant. Additionally, these formats display high surface area per unit volume, which leads to quick drug release times, a feature that is antithetical to the goal of drug delivery. Furthermore, the amount of drug that can be loaded into the above mentioned formats is somewhat limited. Some of these formats cannot be used in conditions which in addition to drug delivery, also require mechanical support.

The present invention provides a fiber composition that does not possess the disadvantages of the drug delivery formats known in the prior art.

SUMMARY OF THE INVENTION

The present invention relates to fiber compositions comprising gels or hydrogels. The invention further relates to the composition of a gel or hydrogel loaded biodegradable fiber and methods of fabricating such fibers. The present invention further provides tissue engineering and drug-delivery compositions and methods wherein three-dimensional matrices for growing cells are prepared for in vitro and in vivo use. The invention also relates to methods of manipulating the rate of therapeutic agent release by changing both the biodegradable polymer properties as well as altering the properties of the incorporated gel or hydrogel.

An embodiment of the invention provides a drug delivery composition comprising at least one fiber, wherein said fiber comprises a first component and a second component, and wherein said first component is a biodegradable polymer and said second component is selected from the group consisting of a gel and a hydrogel. Another embodiment of the invention provides a drug delivery composition comprising a fiber, wherein said fiber comprises a first component and a second component, and wherein said first component is a biodegradable polymer and said second component is water, and further wherein said water is present as an inner core. A further embodiment of the invention provides a drug delivery composition comprising a fiber, wherein said fiber comprises an emulsion consisting essentially of a gel or hydrogel. An embodiment of the invention provides drug delivery composition comprising a fiber, wherein said fiber comprises a first component, is and wherein said first component is a gel or hydrogel and further wherein said fiber comprises a hollow bore. An embodiment of the invention provides a scaffold composition comprising one or more fibers, wherein said fibers comprise a first component and a second component, and wherein said first component is a biodegradable polymer and said second component is selected from the group consisting of a gel and a hydrogel. Embodiments of the invention also provide methods of manufacturing the fibers of the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The drawings are not intended to limit the scope of the invention.

DESCRIPTION OF ILLUSTRATIVE EMBODIMENTS

Figure 1A:
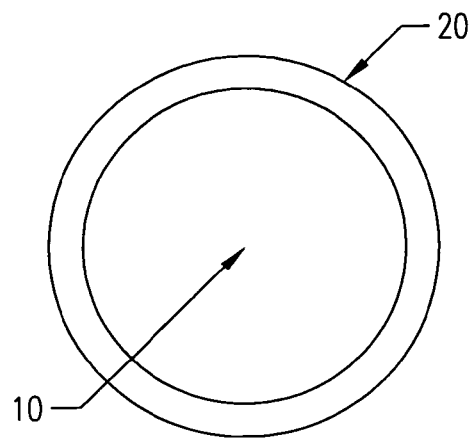
FIG. 1A depicts a bicomponent fiber with a water bore (10) and a wall comprising a hydrophobic polymer (20).
Figure 1B:
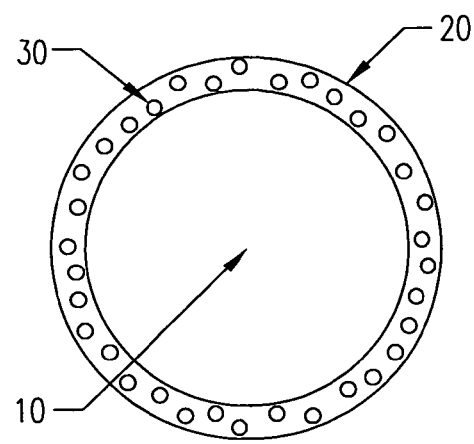
FIG. 1B depicts a bicomponent fiber with a water bore (10), a wall comprising a hydrophobic polymer (20) and a water emulsion (30).
Figure 1C:
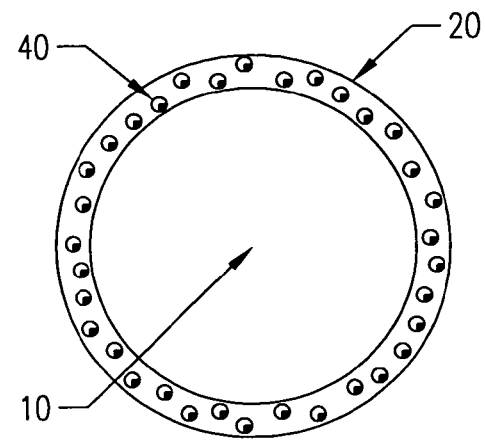
FIG. 1C depicts a bicomponent fiber with a water bore (10), a wall comprising a hydrophobic polymer (20), and a gel or hydrogel emulsion (40).
Figure 1D:
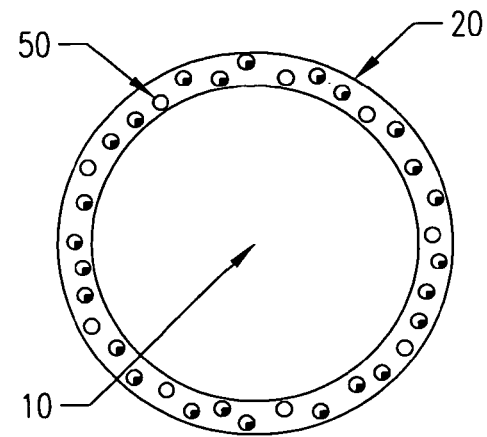
FIG. 1D depicts a bicomponent fiber with a water bore (10), a wall comprising a hydrophobic polymer (20), and both water and gel or hydrogel emulsions (50).
Figure 2A:
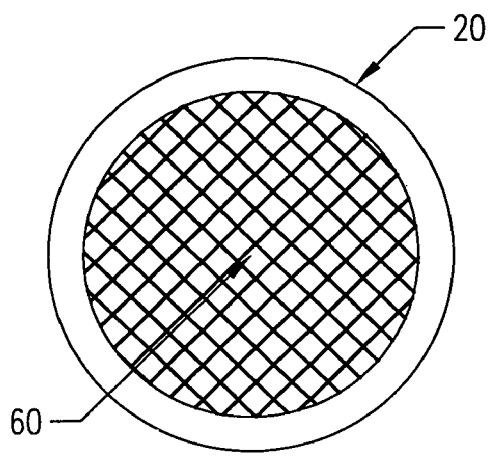
FIG. 2A depicts a bicomponent fiber with a gel or hydrogel bore (60) and a wall comprising a hydrophobic polymer (20).
Figure 2C:
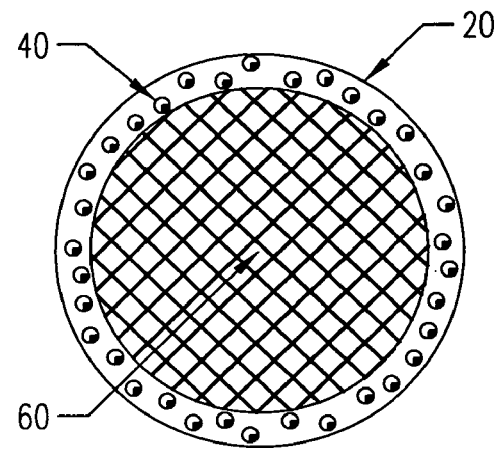
FIG. 2C depicts a bicomponent fiber with a gel or hydrogel bore (60), a wall comprising a hydrophobic polymer (20), and a gel or hydrogel emulsion (40).
Figure 2B:
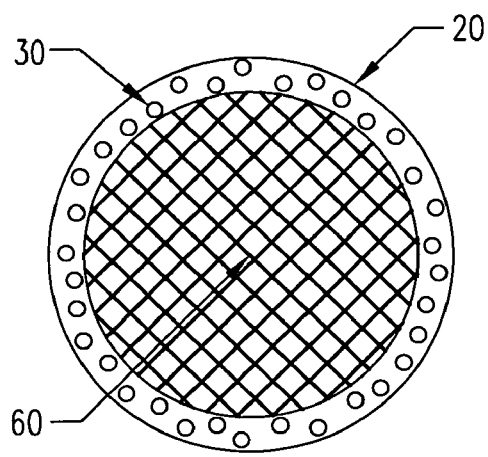
FIG. 2B depicts a bicomponent fiber with a gel or hydrogel bore (60), a wall comprising a hydrophobic polymer (20), and a water emulsion (30).
Figure 2D:
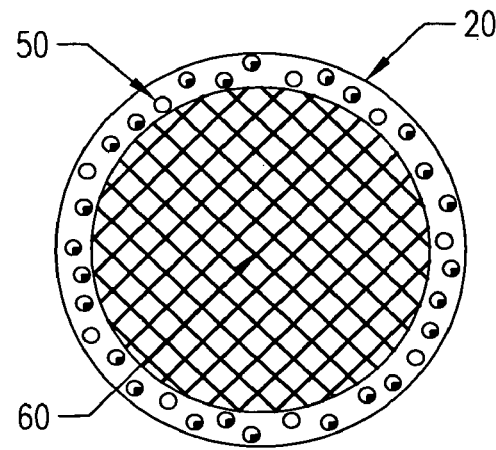
FIG. 2D depicts a bicomponent fiber with a gel or hydrogel bore (60), a wall comprising a hydrophobic polymer (20) and both water emulsions and gel or hydrogel emulsions (50).
Figure 3A:
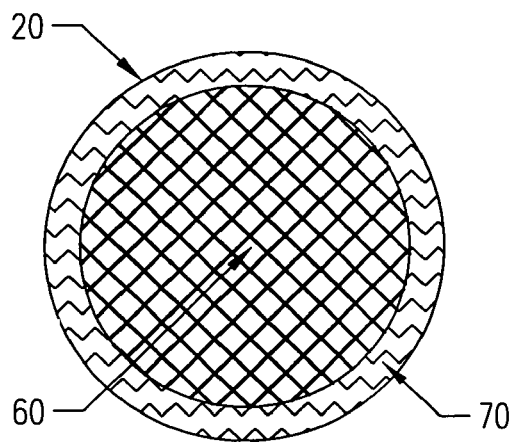
FIG. 3A depicts a bicomponent fiber with a gel or hydrogel bore (60) and a wall comprising a hydrophobic polymer (20) that comprises a drug (70).
Figure 3C:
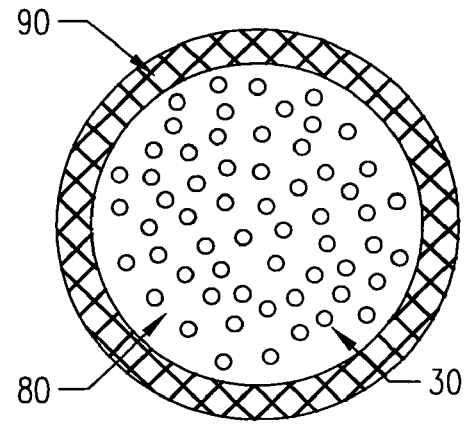
FIG. 3C depicts a bicomponent fiber with a polymer bore (80) comprising a water emulsion (30) that is surrounded by a gel or hydrogel wall (90).
Figure 3B:
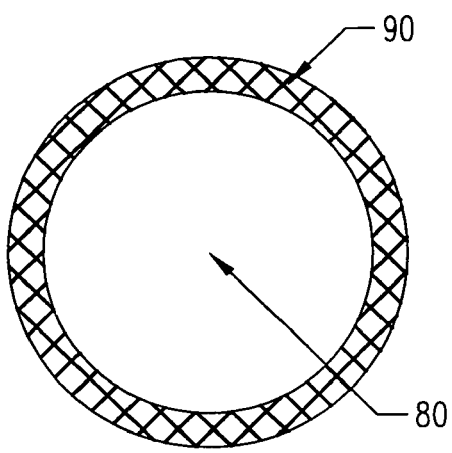
FIG. 3B depicts a bicomponent fiber with a polymer bore (80) surrounded by a gel or hydrogel wall (90).
Figure 3D:
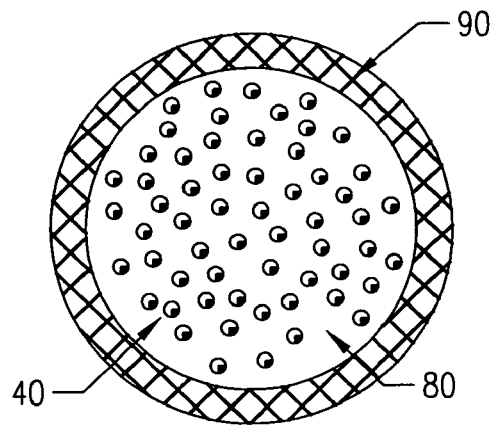
FIG. 3D depicts a bicomponent fiber with a polymer bore (80) comprising a gel or hydrogel emulsion (40) that is surrounded by a gel or hydrogel wall (90).
Figure 4A:
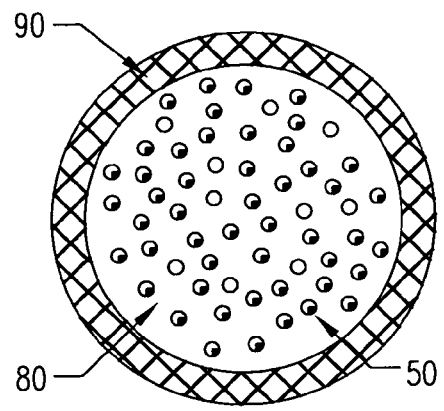
FIG. 4A depicts a bicomponent fiber with a polymer bore (80) comprising a water emulsion and a gel or hydrogel emulsion (50) that is surrounded by a gel or hydrogel wall (90).
Figure 4C:
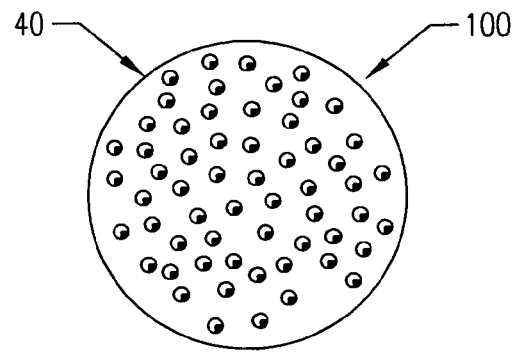
FIG. 4C depicts a monofilament fiber comprising a hydrophobic polymer (100) 30 and a gel or hydrogel emulsion (40).
Figure 4B:
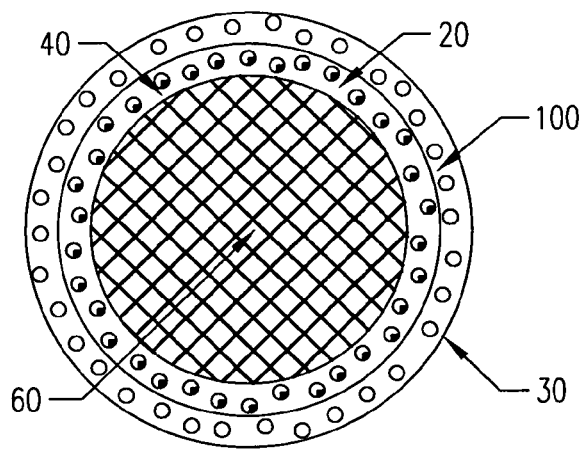
FIG. 4B depicts a multicomponent fiber with a gel or hydrogel bore (60) surrounded by two hydrophobic polymer walls (20 and 100), with the outer polymer wall comprising a water emulsion (30) and the inner polymer wall comprising a gel or hydrogel emulsion (40).
Figure 4D:
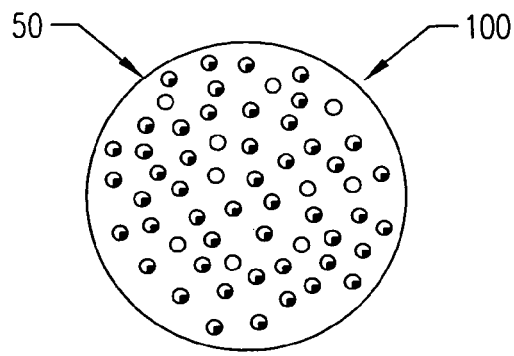
FIG. 4D depicts a monofilament fiber comprising a hydrophobic polymer (100) and a water emulsion and a gel or hydrogel emulsion (50).
Figure 5A:
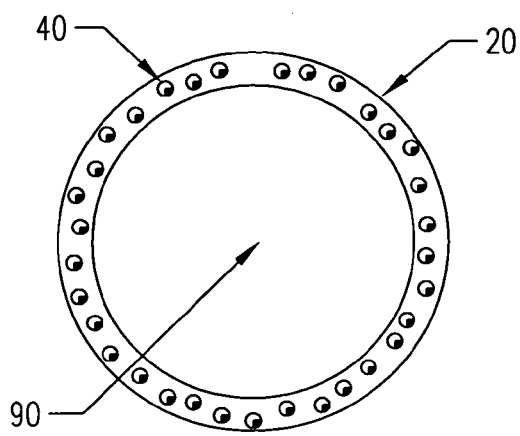
FIG. 5A depicts a bicomponent fiber with a hydrophobic polymer bore (90), and a wall comprising a hydrophobic polymer (20) that comprises a gel or hydrogel emulsion (40).
Figure 5C:
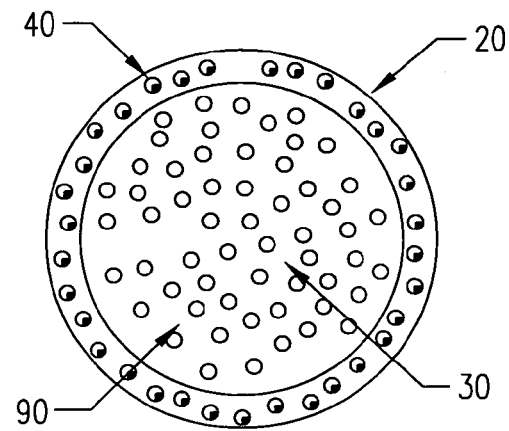
FIG. 5C depicts a bicomponent fiber with a hydrophobic polymer bore (90) comprising a water emulsion (30) and a wall comprising a hydrophobic polymer (20) that comprises a gel or hydrogel emulsion (40).
Figure 5B:
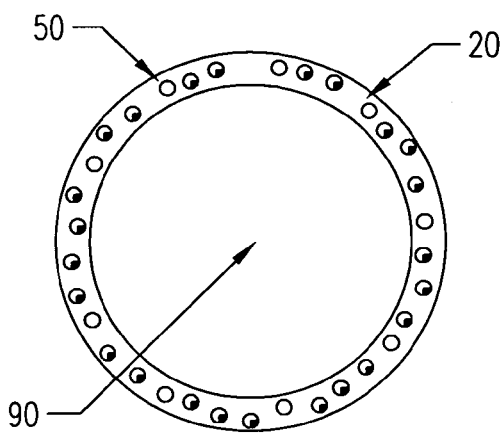
FIG. 5B depicts a bicomponent fiber with a hydrophobic polymer bore (90) and a wall comprising a hydrophobic polymer (20) comprising a water emulsion and a gel or hydrogel emulsion (50).
Figure 5D:
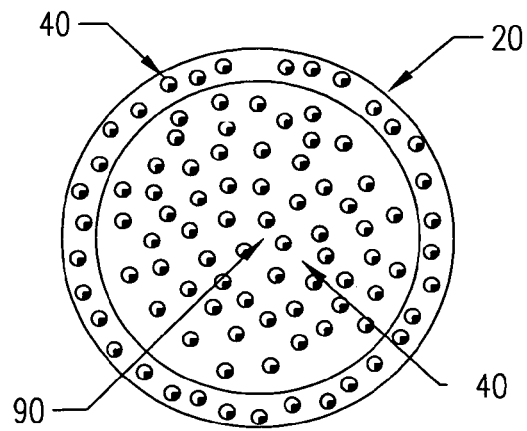
FIG. 5D depicts a bicomponent fiber with a hydrophobic polymer bore (90) comprising a gel or hydrogel emulsion (40) and a wall comprising a hydrophobic polymer (20) that comprises a gel or hydrogel emulsion (40).
Figure 6A:
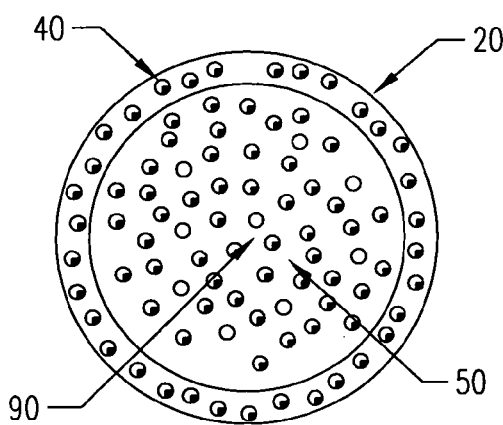
FIG. 6A depicts a bicomponent fiber with a hydrophobic polymer bore (90) comprising a water emulsion and a gel or hydrogel emulsion (50) and a wall comprising a hydrophobic polymer (20) that comprises a gel or hydrogel emulsion (40).
Figure 6C:
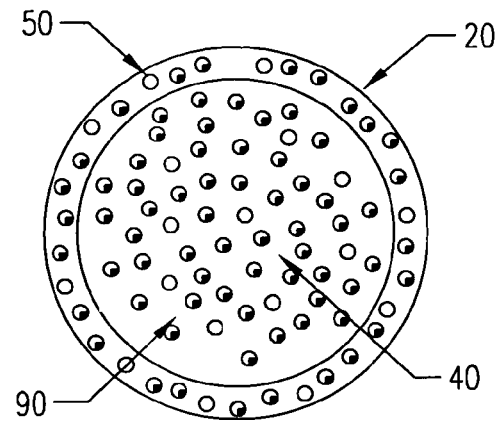
FIG. 6C depicts a bicomponent fiber with a hydrophobic polymer bore (90) comprising a gel or hydrogel emulsion (40) and a wall comprising a hydrophobic polymer (20) comprises a water emulsion and a gel or hydrogel emulsion (50).
Figure 6B:
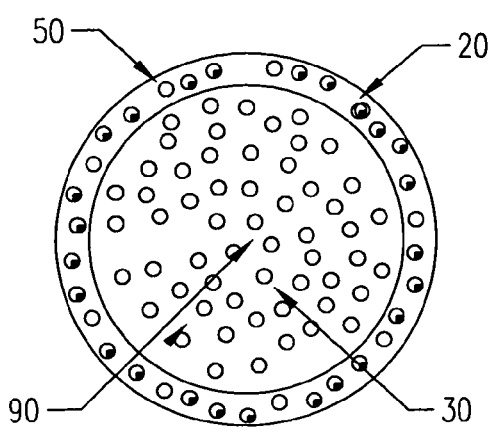
FIG. 6B depicts a bicomponent fiber with a hydrophobic polymer bore (90) comprising a water emulsion (30) and a wall comprising a hydrophobic polymer (20) that comprises a water emulsion and a gel or hydrogel emulsion (50).
Figure 6D:
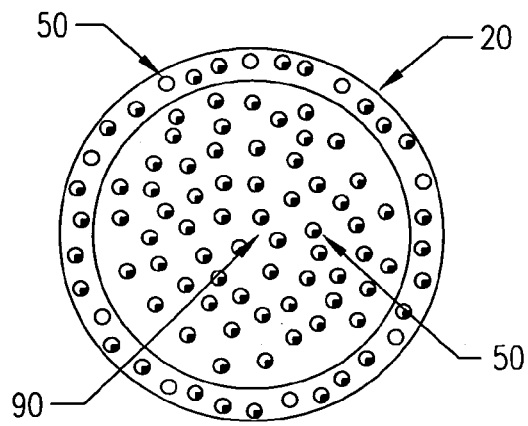
FIG. 6D depicts a bicomponent fiber with a hydrophobic polymer bore (90) comprising both water and gel or hydrogel emulsions (50) and a wall comprising a hydrophobic polymer (20) comprising both water and gel or hydrogel emulsions (50).

An embodiment of the invention provides a drug delivery composition comprising at least one fiber, wherein said fiber comprises a first component and a second component, and wherein said first component is a biodegradable polymer and said second component is selected from the group consisting of a gel and a hydrogel. Another embodiment of the invention provides a drug delivery composition comprising a fiber, wherein said fiber comprises a first component and a second component, and wherein said first component is to a biodegradable polymer and said second component is water, and further wherein said water is present as an inner core. A further embodiment of the invention provides a drug delivery composition comprising a fiber, wherein said fiber comprises an emulsion consisting essentially of a gel or hydrogel. An embodiment of the invention provides drug delivery composition comprising a fiber, wherein said fiber comprises a first component, and wherein said first component is a gel or hydrogel and further wherein said fiber comprises a hollow bore. An embodiment of the invention provides a scaffold composition comprising one or more fibers, wherein said fibers comprise a first component and a second component, and wherein said first component is a biodegradable polymer and said second component is selected from the group consisting of a gel and a hydrogel. Embodiments of the invention also provide methods of manufacturing the fibers of the present invention.

An embodiment of the invention provides a bi-component fiber where the inner bore of the fiber, i.e., inside diameter of the fiber, comprises a gel or hydrogel and the outer wall of the fiber comprises a biodegradable polymer. As used herein, the term "gel" refers to a colloidal system with at least two phases, one of which forms a continuous three-dimensional network that acts as an elastic solid. As used herein, the term "hydrogel" refers to a colloid in which a dispersed phase (colloid) is combined with a continuous phase (water) to produce a viscous jellylike product.

An alternate embodiment of the invention provides the inverse of the above, i.e. where the outer wall comprises a gel or hydrogel and the inner bore comprises a biodegradable polymer fiber.

Another embodiment of the invention provides a monofilament fiber where a hydrogel or gel is dispersed randomly throughout the biodegradable polymer layer(s). This configuration results in distinct phase separation where the biodegradable polymer fiber constitutes a continuous phase and the gel or hydrogel constitutes a disperse phase. As used herein, a "continuous phase" refers to the liquid in a disperse system in which solids are suspended or droplets of another liquid are dispersed. As used herein, a "disperse phase" refers to the phase of a disperse system consisting of particles or droplets of one system dispersed through another system.

In certain embodiments, where the gel or hydrogel concentration is zero, a water bored fiber is provided i.e., a fiber in which water is present within the inside diameter of the fiber. In this case, water, optionally in combination with other materials, comprises the inner core of the fiber and the biodegradable polymer fiber comprises the surrounding sheath of the fiber. In an alternate embodiment, the biodegradable polymer fiber sheath comprises a dispersion of gel or hydrogel. In another embodiment, the biodegradable polymer fiber sheath comprises a dispersion of water in place of a dispersion of gel or hydrogel. In other embodiments, the biodegradable polymer fiber sheath comprises a dispersion of water together with a dispersion of gel and hydrogel.

In an embodiment of the invention, the above described fibers are combined with fibers of similar composition. In other embodiments, fibers of dissimilar type and composition are combined.

In an embodiment, a therapeutic agent is incorporated into one or more of the above described fibers, present individually or in combination. In other embodiments, a drug is incorporated into one or more of the above described fibers, present individually or in combination.

In certain embodiments of the invention, a layer of a fiber circumscribes a layer of an adjacent inner fiber. The inner fiber is approximately centered within the outer fiber. In certain embodiments, one or more of the layers of the circumscribed fibers comprise a hydrogel or a gel in the wall of the fiber or in the bore of the fiber. In additional embodiments, a gel or a hydrogel is incorporated as a dispersed phase within the biodegradable polymer of one or more layers of the fibers. Additional embodiments of the invention provide multi-layered fibers, where each layer comprises varying compositions of gels, hydrogels and therapeutic agents. Certain embodiments of the invention provide fibers comprising more than one kind of therapeutic agent within its one or more layers.

The invention further relates to methods of manipulating the rate of therapeutic agent release by changing both the biodegradable polymer properties as well as altering the properties of the incorporated gel or hydrogel. A therapeutic agent-loaded fiber is suitable for implantation in animals, or more preferably in humans as either single strands for use as a therapeutic agent delivery vehicles, or together with other fibers (of either similar or different type) for the formation of a fiber-based scaffold for use in tissue engineering, wound healing, regenerative medicine, or other medically related applications. These fibers may also be used outside the body to create scaffolds for cell culture, tissue culture, or in vitro organogenesis, wherein specific three-dimensional structures of these fibers may be woven, knitted, braided, used as a non-woven mesh, or maintained as parallel, non-parallel, twisted or random arrays for the creation of complex three-dimensional scaffolds. As each fiber within said fiber scaffold might be loaded with different therapeutic agents, and each with a different release kinetics profile, it may be possible to induce specific cell growth into specific regions of the scaffold. This provides the ability to create complicated three-dimensional biological architecture by deliberate placement of specific fibers at specific locations within the fiber scaffold. These three dimensional biological structures may or may not be biomemetic in their design. By the same means, it is possible to release different therapeutic agents to one section of the cell culture, tissue culture, or organoid than to another within the same sample.

This type of complex three-dimensional fiber scaffold may also be implanted into an animal, or a human to induce specific biological responses at different locations within said fiber scaffold. This is accomplished by designing the fiber scaffold such that fibers with specific therapeutic agents and specific release profiles are placed at specific locations within the scaffold. This enables the control of both temporal and spatial therapeutic agent delivery from the fiber scaffold.

"Defined nonhomogeneous pattern" in the context of the current application means the incorporation of specific fibers into a scaffold matrix such that a desired three dimensional distribution of one or more therapeutic agents within the scaffold matrix is achieved. The distribution of therapeutic agents within the fibers, and possibly within their centers, controls the subsequent spatial distribution within the interstitial medium of the matrix scaffold following release of the agents from the polymer fibers. In this way, the spatial contours of desired concentration gradients can be created within the three dimensional scaffold structure and in the immediate surroundings of the scaffold matrix. Temporal distribution is controlled by the polymer composition and gel or hydrogel composition of the fiber and by the use of multi-layers within a fiber.

One aspect of the present invention is a biocompatible implant composition comprising a scaffold of biodegradable polymer fibers. In various embodiments of the present invention, the distance between the fibers may be about 20 microns, about 70 microns, about 90 microns, about 100 microns, about 120 microns, about 140 microns, about 160 microns, about 180 microns, about 200 microns, about 220 microns, about 240 microns, about 260 microns, about 280 microns, about 300 microns, about 320 microns, about 340 microns, about 360 microns, about 380 microns, about 400 microns, about 450 microns or about 500 microns. In various embodiments the distance between the fibers may be less than 50 microns or greater than 500 microns.

Additionally, it is envisioned that in various embodiments of the invention, the fibers will have a diameter of about 20 microns, about 40 microns, about 60 microns, about 80 microns, about 100 microns, about 120 microns, about 140 microns, about 160 microns, about 180 microns, about 200 microns, about 220 microns, about 240 microns, about 260 microns, about 280 microns, about 300 microns, about 320 microns, about 340 microns, about 360 microns, about 380 microns, about 400 microns, about 450 microns or about 500 microns (including intermediate lengths). In various embodiments the diameter of the fibers may be less than about 20 microns or greater than about 500 microns. Additionally, large fibers with diameters up to 3.5 cm are envisioned for certain embodiments. Preferably, the diameter of the fibers will be from about 60 microns to about 500 microns.

In another embodiment of the present invention, the fibers or a subset of fibers, contain one or more therapeutic agents such that the concentration of the therapeutic agent or agents varies along the longitudinal axis of the fibers or subset of fibers. The concentration of the active agent or agents may vary linearly, exponentially or in any desired fashion, as a function of distance along the longitudinal axis of a fiber. The variation may be monodirectional, that is, the content of one or more therapeutic agents decreases from the first end of the fibers or subset of the fibers to the second end of the fibers or subset of the fibers. The content may also vary in a bidirection fashion, that is, the content of the therapeutic agent or agents increases from the first ends of the fibers or subset of the fibers to a maximum and then decreases towards the second ends of the fibers or subset of the fibers.

In certain embodiments of the present invention, a subset of fibers comprising the scaffold may contain no therapeutic agent. For fibers that contain one or more therapeutic agents, the agent or agents may include: a growth factor, an immunodulator, a compound that promotes angiogenesis, a compound that inhibits angiogenesis, an anti-inflammatory compound, an antibiotic, a cytokine, an anti-coagulation agent, a procoagulation agent, a chemotactic agent, agents that promotes apoptosis, an agent that inhibits apoptosis, a mitogenic agent, a radioactive agent, a contrast agent for imaging studies, a viral vector, a polynucleotide, therapeutic genes, DNA, RNA, a polypeptide, a glycosaminoglycan, a carbohydrate, a glycoprotein. The therapeutic agents may also include those drugs that are to be administered for long-term maintenance to patients such as cardiovascular drugs, including blood pressure, pacing, anti-arrhythmia, beta-blocking drugs, and calcium channel based drugs. Therapeutic agents of the present invention also include anti-tremor and other drugs for epilepsy or other movement disorders. These agents may also include long-term medications such as contraceptives and fertility drugs. They could comprise neurologic agents such as dopamine and related drugs as well as psychological or other behavioral drugs. The therapeutic agents may also include chemical scavengers such as chelators, antioxidants and nutritional agents. Wherein the therapeutic agent promotes angiogenesis, that agent may be vascular endothelial growth factor. The therapeutic agents may be synthetic or natural drugs, proteins, DNA, RNA, or cells (genetically altered or not). As used in the specification and claims, following long-standing patent law practice, the terms "a" and "an," when used in conjunction with the word "comprising" or "including" means one or more.

In general, the present invention contemplates the use of any drug incorporated in the biodegradable polymer fibers of the invention. The word "drug" as used herein is defined as a chemical capable of administration to an organism, which modifies or alters the organism's physiology. More preferably the word "drug" as used herein is defined as any substance intended for use in the treatment or prevention of disease. Drug includes synthetic and naturally occurring toxins and bioaffecting substances as well as recognized pharmaceuticals, such as those listed in "The Physicians Desk Reference," 471st edition, 5 pages 101-321; "Goodman and Gilman's The Pharmacological Basis of Therapeutics" 8th Edition (1990), pages 84-1614 and 1655-1715; and "The United States Pharmacopeia, The National Formulary", USP XXII NF XVII (1990), the compounds of these references being herein incorporated by reference. The term "drug" also includes compounds that have the indicated properties that are not yet discovered or available in the U.S. The term "drug" to includes pro-active, activated, and metabolized forms of drugs. Tissue stimulating factors are also included such as: dimers of Platelet Derived Growth Factor (PDGF), insulin-like growth factor-1 (IGF-1), IGF-2, basic Fibroblast Growth Factor (bFGF), acidic FGF, Vascular Endothelial Cell Growth Factor (VEGF), Nerve Growth Factor (NGF), Neurotrophic Factor 3 (NT-3), Neurotrophic Factor 4 (NT-4), Brain Derived Neurotrophic Factor (BDNF), Endothelial Growth Factor (EGF), Insulin, Interleukin 1 (Il-1), Tumor Necrosis Factor alpha (TNFa.), Connective Tissue Growth Factor (CTGF), Transforming Growth Factor alpha (TGFa), and all other growth factors and cytokines, as well as parathyroid hormone (PTH), prostaglandin such as Prostaglandin E-1 and Prostaglandin E-2, Macrophage Colony Stimulating Factor (MCSF), and corticosteroids such as dexamethasone, prednisolone, and corticosterone.

The present invention also contemplates the use of hydrogel forming material within the core of the fibers. Hydrogels are structurally stable, synthetic polymer or biopolymer matrices that are highly hydrated. These materials may absorb up to thousands of times their weight in water (Hoffman, A. S., Advanced Drug delivery Reviews, 43 (2000), 3-12). Hydrogels can be classified into two broad categories: reversible or physical and irreversible or chemical. The networks in physical gels are held together by molecular entanglements and/or secondary forces including ionic, H-bonding or hydrophobic forces. Physical hydrogels are characterized by significant changes in the rheological properties as a function of temperature, ionic concentration, and dilution. Chemical gels, also called permanent gels, are characterized by chemically crosslinked networks. When crosslinked, these gels reach an equilibrium swelling level in aqueous solutions which depends mainly on the crosslink density.

The preparation of hydrogels can be achieved by a variety of methods well known to those of ordinary skill in the art. Physical gels can be formed by: heating or cooling certain polymer solutions (cool agarose, for example), using freezethaw cycles to form polymer microcrystals, reducing the solution pH to form a H-bonded gel between two different polymers in the same aqueous solution, mixing solutions of a polyanion and a polycation to form a complex coacervate gel, gelling a polyelectrolyte solution with a multivalent ion of opposite charge, reticulation of linear polymers, grafting of synthetic polymers onto naturally occurring macromolecules, and chelation of polycations (Hoffman, A. S., Advanced Drug delivery Reviews, 43 (2000), 3-12). Chemical gels can be created by crosslinking polymers in the solid state or in solution with radiation, chemical crosslinkers like glutaraldehyde, or multifunctional reactive compounds. They can also be made by copolymerizing a monomer and a crosslinker in solution, is copolymerizing a monomer and a multifunctional macromer, polymerizing a monomer within a different solid polymer to form an IPN gel, or chemically converting a hydrophobic polymer to a hydrogel (Hoffman, A. S., Advanced Drug delivery Reviews, 43 (2000), 3-12); Hennick, W. F. and van Nostrum, C. F., Advanced Drug Delivery Reviews, 54 (2002), 13-26.

The present invention contemplates the use of hydrogel precursor materials and non-gelling proteins and polysaccharides within the bore of the fibers. Hydrogel precursor materials are the same materials as those that form hydrogels, but they are not exposed to the agents or conditions that normally gel the materials, or can be other proteins and polysaccharides that form gels but not hydrogels. For example, alginate salts, such as sodium alginate, are gelled in the presence of divalent cations, such as calcium, while other materials create hydrogels via a change in pH or temperature. Certain embodiments of the invention comprise the use of precursor materials that are never gelled. Other embodiments of the invention comprise the use of precursor materials in the fabrication process that later may form gels or hydrogels. The formation of gels or hydrogels in the fiber layer may take place as a part of the fiber fabrication process, after the fiber has been fabricated, or after the application of an appropriate type of external stimuli, including placing the fiber in vitro or in vivo. The terms "gel" or "hydrogel" as used herein is intended to include the formed gel or hydrogel as well as the appropriate precursor molecules involved in the formation of gels and hydrogels.

The biodegradable polymer used for fiber construction may be a single polymer or a co-polymer or blend of polymers and may comprise poly(L-lactic acid), poly(DL-lactic acid), polycaprolactone, poly(glycolic acid), polyanhydride, or natural polymers or polypeptides, such as reconstituted collagen or spider silk and polysaccharides.

The fibers of the claimed invention are manufactured using wet or dry/wet (dry jet wet) spinning. Each method affects the final properties of the fiber being constructed. Wet spinning is a process in which a polymeric material is extruded into a liquid bath containing a coagulant. The coagulant is typically comprised of a non-solvent for the polymer that is miscible with the solvent in the polymer solution, but it can also contain a solvent/non-solvent mixture. In dry jet wet spinning, the polymer solution is first exposed to an air gap before entering the coagulation bath.

In an embodiment of the invention, the fiber comprises a plurality of co-axial layers of biodegradable polymers. The drug delivery fiber of the present invention may be implanted into many sites in the body including dermal tissues, cardiac tissue, soft tissues, nerves, bones, and the eye. Ocular implantation has particular use for treatment of cataracts, diabetically induced proliferative retinopathy and non-proliferative retinopathy, glaucoma, and macular degeneration.

A further aspect of the present invention is a method of producing a fiber-scaffold for preparing an implant capable of controlling the spatial and temporal concentration of one or more therapeutic agents. This method generally comprises forming biodegradable polymer fibers into a three dimensional fiber-scaffold. The biodegradable polymer fibers contain one or more therapeutic agents. The therapeutic agent or agents are distributed in the fiber-scaffold in a defined non-homogeneous pattern.

In certain embodiments of the invention, gels and hydrogels comprised in the fiber layers may exist at infinitely dilute concentrations, i.e., the concentration of gel or hydrogel is zero, and water is used with or without other substances and/or active agents, including therapeutic agents, in place of the gel or hydrogel.

In one embodiment of this invention, the preferred material for the hydrogel contained in the bore of the fiber will be alginate or modified alginate material. Alginate molecules are comprised of (1-4)-linked/3-D-mannuronic acid (M units) and (α-L-guluronic acid (G units) monomers, which vary in proportion and sequential distribution along the polymer chain. Alginate polysaccharides are polyelectrolyte systems that have a strong affinity for divalent cations (e.g. $Ca^{2+}$, $Sr^{2+}$, $Ba^{2+}$) and form stable hydrogels when exposed to these molecules. The biodegradable polymer is poly(L-lactic acid) (PLLA). In an embodiment, the alginate is contained as the inner core and the PLLA is the outer sheath. The concentration of alginate is in the range of 0.25 w/v % to 100 w/v % (i.e., g/100 ml water), preferably in the range of 0.75 w/v % to 20 w/v %, and most preferably at a concentration of 1 w/v %. The source and composition of alginate directly affects its usable concentration.

In another embodiment of this invention, the PLLA sheath surrounding the inner gel or hydrogel core comprises a cocktail of PLLA polymers of different molecular weights as a means of increasing the degradation rate. The proportions of the PLLA polymers and the range of the polymer molecular weights can vary. In an exemplary embodiment, the polymer cocktail comprises 80% by weight of a PLLA polymer of Mw=100,000 Daltons; 15% by weight of a polymer of Mw=2,000 Daltons; and 5% by weight of a polymer Mw=300,000 Daltons.

In another embodiment of the invention, the PLLA sheath surrounding the inner gel or hydrogel core is comprised of two phases, a continuous phase comprising a biodegradable polymer and a dispersed phase comprising an aqueous phase stabilized by a surfactant. The aqueous phase may optionally comprise therapeutic agents. The amount of the dispersed phase ranges from about 0% to about 85% by weight relative to the weight of the fiber. In a preferred embodiment the amount of the dispersed phase ranges from about 33% to about 50% by weight relative to the weight of the fiber. As the ratio of the dispersed phase increases, so does the rate of degradation of the polymer. This leads to increased release rates of loaded therapeutic agents.

In an embodiment of this invention, agents that are designed to degrade the gel or hydrogel are loaded into the dispersed aqueous phase of the biodegradable polymer component of the fiber (as described above). This agent is released into the gel or hydrogel slowly over time to break down the gel or hydrogel. This increases therapeutic agent release rates. In addition, many of the potential gels and hydrogels are not directly biodegradable within animals, or more especially humans. Therefore, this planned degradation helps the body to eliminate the gels or hydrogels when they are no longer needed.

In an embodiment, the alginate is gelled internally by the addition of gelling agents added directly to the alginate solution. Typical gelling agents include calcium chloride, calcium carbonate, calcium-EDTA (Ethylene Diamine Tetracetic Acid), or other compounds containing bivalent cations that are well known to those skilled in the art. The concentration of the gelation agent ranges from about 5 mM to about 100 mM, more preferably from about 12 mM to about 50 mM, and most preferably from about 15 mM to 30 mM. The range chosen is determined by desired hydrogel properties. If not readily soluble at neutral pH, the gelling agent is typically activated by a drop in pH of the solution. This acidification can be achieved through a number of acids or lactones. This list includes, but is not limited to, citric acid, hydrochloric acid, D-glucono-delta-lactone, and glacial acetic acid.

In another embodiment, the gel or hydrogel is gelled externally by incorporating the gelling agent source into the biodegradable fiber. Alternately, the gelling agent source is added to a water phase that is loaded into one or more layers of the biodegradable polymer. In this way, the gelling agent is slowly released into the gel or hydrogel as the fiber degrades. In certain embodiments, as the fiber degrades and becomes weaker and more porous, the gel becomes more tightly cross-linked. In this way, it may be possible to continuously alter the release rate as the fiber degrades. Release rates tend to increase as the polymer becomes more porous, in this case, this trend would be offset by the gel becoming more tightly cross-linked, hence retarding release rates through the gel or hydrogel as the fiber degrades.

In another embodiment, the gelling agent is soluble in the polymer solvent and is mixed with the polymer solution at the time of fiber fabrication. In this embodiment, rather than the gelling agent being maintained in an aqueous phase, it is molecularly mixed with the polymer. The same net effect of releasing the gelling agent into the gel or hydrogel slowly as the fiber degrades. This embodiment allows the use of organically soluble sources of gelling agents.

In another embodiment, the gelation agents are carried within the alginate solution that are activated over time, such as within liposheres, microspheres, nanoparticles or other encapsulants that are activated later. These may be slowly activated over time, or purposefully activated by some external event. This will result in the gel either being strengthened, or maintained over time.

In another embodiment of the invention, the gel or hydrogel is the exterior sheath and the biodegradable polymer is the interior core. In this embodiment the gelling agent is in the coagulating bath, which would be an external gelation.

The present invention provides compositions and methods to create single, drug releasing fibers as well as the composition and methods to create a heterogeneous, woven, knitted, braided, non-woven, twisted, parallel array or random three-dimensional fiber scaffold for growing cells in tissue engineering applications. These scaffolds can be used in vitro and in vivo, and due to their heterogeneity can create both spatial and temporal distributions of therapeutic agents. In this invention, therapeutic agents may include drugs, proteins, peptides, mono- and di-saccharides, polysaccharides, glycoproteins, DNA, RNA, viruses, or other biological molecules of interest. The term therapeutic agent in this invention also includes radioactive materials used to help destroy harmful tissues such as tumors in the local area, or to inhibit growth of healthy tissues, such as in current stent applications; or markers to be used in imaging studies.

A. Three Dimensional Fiber Scaffolds

To create the heterogeneous scaffolds of the present invention, the therapeutic agents are encapsulated into individual fibers of the matrix by methods to be described herein. The therapeutic agents are released from each individual fiber slowly, and in a controlled manner. The fiber format has many advantages as a drug delivery platform over other slow drug-releasing agents known to those familiar in the art such as microspheres, porous plugs or patches. The primary advantage of fibers is that they can provide complex three-dimensional woven, or non-woven scaffolding, with or without patterning, to allow cells to attach, spread, differentiate, and mature into appropriately functioning cells. Because they can form patterns, a "smart scaffold" can be produced to induce cells of specific types to migrate to specific regions of the scaffold due to specific chemotactic factors being released. This scaffold mimics the function of the extracellular matrix material both during embryological development and in post-embryological tissues. Additionally, filaments could be formed into a unique scaffold that provides a growth substrate for tissue repair or reconstruction that is not reminiscent of a natural like structure.

Because of the ability to weave patterns to induce appropriate cell types into specific regions, it is possible to incorporate strands that will induce the formation of blood vessels into the fabric. This may be accomplished by providing fibers that release growth factors such as vascular endothelial growth factor (VEGF). By appropriate spacing of VEGF containing-fibers into the weave pattern, large tissues may be engineered, and the cells in such tissues can be provided with a sufficient blood supply and thereby receive oxygen and nutrients and enable the removal of waste products.

Fibers also have the advantage of providing the body with short term mechanical is support in such applications as stents, wherein the polymer fiber can maintain the lumen of any tubular body, such as arteries, veins, ducts (e.g. bile duct, ureter, urethra, trachea, etc.), organs of the digestive track such as esophagus, intestine, colon, and connective tissue such as tendons, ligaments, muscle and bone. The fibers provide a useful structure to support mechanical strength or tension during the healing process. Fibers may also be useful to promote neural regeneration or reconstruction of nerves or spinal cord.

B. Fiber Formats

There are a large number of combinations and variations within the scope of this invention. This invention covers gel or hydrogel combinations with a biodegradable polymer fiber in a multi-layer, multi-component format, where each layer is fully contained within the next outer layer, and the inner layer is generally centered within the outer layer. These layers can be comprised of different gels or hydrogels, or different biodegradable polymers.

This invention also includes the use of gels or hydrogels as a dispersed phase within biodegradable polymer layer, wherein the continuous phase is the biodegradable polymer phase. The dispersed phase may be stabilized by either an internal or external surfactant.

In the case of the dispersed gel or hydrogel within the biodegradable polymer layer, and in the case of the gel or hydrogel layer being interior to a biodegradable polymer layer, an allowable special case is that the concentration of the hydrogel is zero. This means that water may be used (with or without the inclusion of other substances) in the place of the gel or hydrogel.

As an additional special case, it may be possible for the polymer concentration in the innermost core to be zero, in which case the solvent normally used with the polymer is replaced by a non-solvent. In this case, the non-solvent core acts as an internal coagulating bath. The result is that a hollow fiber is created. This special case can occur with or without a gel or hydrogel exterior to the biodegradable polymer layer(s) and with or without a dispersed gel, hydrogel or water phase within the biodegradable polymer layer(s).

This leads to a large number of potential combinations. The basic types are external biodegradable polymer with internal gel or hydrogel, and the inverse design, i.e. gel or hydrogel external with the biodegradable polymer as the internal core. In each of these combinations, the biodegradable polymer layer may or may not have a dispersed water, gel or hydrogel phase. Another case is a monofilament fiber with a gel or hydrogel dispersed phase.

C. Release Kinetics of Individual Fibers

Further, there are various means for controlling the release kinetics of the therapeutic agent, thus temporally controlling the release of the therapeutic agent. The following discussion will pertain only to the fiber format wherein the polymer sheath surrounds an inner core of gel or hydrogel. The first point of control for the polymer is to mix low molecular weight polymer in with the higher molecular weight, fiber forming polymers. In this way, the lower molecular weight component is able to rapidly degrade and diffuse from the fiber, making the fiber more porous. This makes the interior therapeutic agents within the gel or hydrogel more accessible. A second means of accelerating the release rate of the fiber is to create a bi-phasic fiber, wherein the continuous phase is the biodegradable polymer, and the dispersed phase is aqueous pockets that are stabilized by a surfactant. As the concentration of the dispersed phase increases, a pathway is created from the outside to the inner gel or hydrogel where the only polymer that must be degraded is between the various pockets of the dispersed aqueous phase. This has the effect of leaving much less polymer to degrade to connect the gel or hydrogel to the outside world, thus accelerating the release of the therapeutic agent. It is also possible for this dispersed aqueous phase to contain the same or a different drug or therapeutic agent. In this case, the drug or therapeutic agent in the dispersed aqueous phase will be released first, followed by the release of the therapeutic agent in the gel or hydrogel. To alter the release kinetics of the drug or therapeutic agent in the polymer fiber wall, it is possible to slightly adapt the above description such that the dispersed phase is now a gel or hydrogel as opposed to being aqueous. In this case, the fluid pathway shortening exists as in the case of an aqueous dispersed phase; however, the connecting pathway must now go through pockets of gel or hydrogel, wherein the diffusion of the therapeutic agent is retarded compared to a purely aqueous pathway. The degree to which the diffusion is retarded is a function of the type of gel or hydrogel, the type and degree of cross-linking, and the concentration of the gel or hydrogel. All of these parameters are is within the control of the entity forming the fiber. It is also possible to control the concentration of the dispersed aqueous or gel phase within the biodegradable polymer as a function of distance along the long axis of the fiber. By this means, it is possible to have different release kinetics at one end of the fiber than at the other, with a defined gradient of release kinetics down the length of the fiber. This change in release kinetics may or may not be combined with a gradient of therapeutic agent concentration. By the same means, it is possible to have the content of the disperse phase vary as a function of distance down the polymer fiber such that at one end the dispersed phase would be for example purely aqueous and at the second end of the fiber, the dispersed phase could be a gel or hydrogel. Other gradients are also possible including varying concentrations of the gel within the disperse phase. Thus a great deal of control is available on the release kinetics of the fiber. Aside from these changes in the polymer wall of the fiber, it is also possible to control the release kinetics from this fiber by altering the type, concentration, and degree of cross-linking within the gel or hydrogel in the core of the fiber, which contains a therapeutic agent.

The ability to dynamically change the release kinetics of the gel or hydrogel being loaded into the core or as a dispersed phase within a biodegradable polymer fiber over the course of the drug delivery period constitutes an important aspect of the invention. This affords unique opportunities that are not possible to be present in other forms of drug delivery from gels or hydrogels. The first means of control available because of the gel being loaded into a biodegradable polymer fiber is the ability of this fiber to release agents known to cross link the gel. In this way, over time, the cross-linking density of the gel actually increases, which will retard the release of the therapeutic agent. This release of the cross linking agent from the biodegradable polymer fiber sheath is itself controllable by means outlined above, i.e. using a cocktail of molecular weights, or changing the concentration of the dispersed aqueous phase. As a special case of the biodegradable polymer fiber sheath is a multi-layer, and multi-component biodegradable polymer sheath. This allows the creation of directional specificity, as well as changes in the release kinetics from each layer of the biodegradable polymer fiber sheath. For example, consider the case of two layers of biodegradable polymer fiber in the sheath. The innermost layer could contain agents that act to cross link the gel or hydrogel core of the fiber, and this layer could be composed of a biodegradable polymer that has a rapid degradation rate. Further, this layer could contain a high degree of dispersed aqueous phase. In this same example, the outermost layer may be composed of a different biodegradable polymer with a different degradation rate, and a different concentration of dispersed aqueous (or gel or hydrogel) dispersed phase, including zero. This example would create a situation where the cross-linking agent would be delivered inwardly to the gel or hydrogel in the core of the fiber over time, thus creating a situation wherein the diffusion coefficient of the therapeutic agent loaded into the gel or hydrogel in the core of the fiber decreases over time.

Another special case is where the polymer fiber contains agents that degrade the gel or hydrogel in the core of the fiber. Using the same logic as explained above, this too creates a situation where the diffusion coefficient of the therapeutic agent in the gel or hydrogel in the core or dispersed within the fiber changes continuously over time. In this case, however, the diffusion rate increases over time. This particular case also has the advantage that the body of the animal or preferably the human into which the fiber is implanted may not have the specific enzymes or other chemical conditions required to degrade the gel or hydrogel. In this case, loading appropriate degradation agents into the wall of the fiber allows the degradation of the gel or hydrogel, and thus aids the clearance of the gel or hydrogel from the host. Again, as described above, the release of the degradation agents is largely controllable by changing properties of the biodegradable polymer layers in the sheath of the fiber.

By these methods, it is seen that the release kinetics of the therapeutic agent from a gel or hydrogel core or dispersed in a sheath of biodegradable polymer fiber is alterable by virtue of the presence of biodegradable polymer sheath.

In the case where the gel or hydrogel is the exterior layer and the biodegradable polymer is the core of the fiber. In this case the biodegradable polymer core may consist of one or more multi-component layers as described above, and again each layer may contain a different concentration of dispersed aqueous or gel or hydrogel phase, which may or may not themselves carry therapeutic agents. The overall release of therapeutic agent(s) from the fiber is controlled by the location of the therapeutic agents, either in the gel or hydrogel exterior, or within the biodegradable polymer core or both. By the same means as described above, the exterior gel or hydrogel release kinetics may be altered by the release of cross-linking, or degrading agents from the biodegradable polymer fiber core. As these agents are released from the biodegradable polymer fiber core, they will alter the properties of the exterior gel or hydrogel, thus decreasing or increasing the diffusion of the therapeutic agent from the exterior gel or hydrogel. For any therapeutic agent(s) within the biodegradable polymer core, the release of these agents is controlled on two levels. First, as explained above the type and molecular weight distribution of the polymer itself changes the release kinetics, as well known to those skilled in the art. In addition to this, the concentration of any dispersed aqueous or gel or hydrogel phase will alter the release from the biodegradable polymer. However, as the gel or hydrogel is surrounding the biodegradable fiber, all therapeutic agents within the biodegradable polymer must diffuse through the gel or hydrogel. Therefore, any changes to the diffusion of the therapeutic agent(s) through the gel or hydrogel also directly affect the release of any therapeutic agents within the core of the fiber. Therefore, in this case, one can change the release kinetics of the fiber by altering both the gel and the biodegradable polymer segments.

If the dispersed phase is a gel or hydrogel that also contains the therapeutic agent, then the release of that therapeutic agent is controllable by the same means of choice of biodegradable polymer, molecular weight distribution, and concentration of the dispersed phase. In addition, the properties of the gel or hydrogel also alter the release of the therapeutic agent from the dispersed phase within the monofilament fiber.

D. Biodegradable Polymers

Preferred polymers for use in the present invention include single polymer, co-polymer or a blend of polymers of poly (L-lactic acid), poly(DL-lactic acid), polycaprolactone, poly (glycolic acid) or polyanhydride. Naturally occurring polymers may also be used such as reconstituted collagen or natural silks. Those of skill in the art will understand that these polymers are just examples of a class of biodegradable polymer matrices that may be used in this invention. Further biodegradable matrices include polyanhydrides, polyorthoesters, and poly(amino acids) (Peppas and Langer, 1994). Any such matrix may be utilized to fabricate a biodegradable polymer matrix with controlled properties for use in this invention. A non-exhaustive list of biodegradable polymers that produce non-toxic degradation products are listed in Table 1.

TABLE 1

Biodegradable polymers

Synthetic

Polypeptides
Polydepsipeptides
Nylon-2/nylon-6 copolyamides
Aliphatic polyesters
    Poly(glycolic acid) (PGA) and copolymers
    Poly(lactic acid) (PLA) and copolymer
    Poly(alkylene succinates)
    Poly(hydroxy butyrate) (PHB)
    Poly(butylene diglycolate) Poly(ε-caprolactone) and copolymers
Polydihydropyrans
Polyphosphazenes
Poly(ortho ester)
Poly(cyano acrylates)

TABLE 1-continued

Biodegradable polymers

Natural

Modified polysaccharides
    cellulose, starch, chitin
Modified proteins
    collagen, fibrin Adapted from Wong and Mooney, 1997.

E. Types of Gels and Hydrogels

In simple terms, a gel is a liquid system that acts like a solid. More technically defined, a gel is a colloidal system with at least two phases, one of which forms a continuous three-dimensional network that acts as an elastic solid. Gel formation through physical, molecular, or chemical association results in an infinite molecular weight for the system. The viscoelastic material formed has a storage modulus, $G'$, that is greater than the loss modulus, $G''$, and both $G'$ and $G''$ are almost independent of frequency. [E. R. Morris, Polysaccharide solution properties: origin, rheological characterization and implications for food systems, Frontiers in Carbohydrate Research 1: Food Applications (R. P. Millane, J. N. BeMiller, and R. Chandrasekaran, eds.), Elsevier, London, 1989, p. 132.] The storage modulus characterizes the rigidity of the sample, while the loss modulus characterizes the resistance of the sample to flow. [Damodaran, Srinivasan, Food Proteins and Their Applications, Food Science and Technology (Marcel Dekker, Inc.); New York Marcel Dekker, Inc., 1997.] Examples are polymer solutions, micellar solutions, microemulsions and, in more recent years, the field has been extended with the large number of organic solvents that are gelled by the presence of small organic molecules at very low concentrations.

A hydrogel is defined as a colloid in which the disperse phase (the colloid) has combined with the continuous phase (water) to produce a viscous jellylike product. [Dictionary of Chemical Terms, 4th Ed., McGraw Hill (1989)]. Hydrogels are able to swell rapidly in excess water and retain large volumes of water in their swollen structures. The polymeric material comprising the hydrogel can absorb more than 20% of its weight in water, though formed hydrogels are insoluble in water and they maintain three-dimensional networks. [Amidon, Gordon L., Transport Processes in Pharmaceutical Systems, Drugs and the Pharmaceutical Sciences; v. 102 New York Marcel Dekker, Inc., 2000]. They are usually made of hydrophilic polymer molecules crosslinked either by chemical bonds or by other cohesion forces such as ionic interaction, hydrogen bonding, or hydrophobic interaction. [J. I. Kroschwitz, Concise Encyclopedia of Polymer Science and Engineering, New York, Wiley, XXIX, p 1341, 1990.]

Hydrogels are elastic solids in the sense that there exists a remembered reference configuration to which the system returns even after being deformed for a very long time.

An organogel is defined as an organic phase with an interlaced polymeric component. Preferred solvents include non-toxic organic solvents including, but not limited to, dimethyl sulfoxide (DMSO), mineral oils and vegetable oils. The term "organogel" was initially used to describe a specific concept of gelation, by a gelatin solution, of a water-in-oil inverse microemulsion (see Luisi et al. Colloid & Polymer Science, 1990, vol. 268, p. 356-374). The term has recently been extended to gelled systems comprising two immiscible phases (water in oil) stabilized in lecithin enriched with phosphatidylcholine and usually hydrogenated (see Willliman et al. Journal of Pharmaceutical Sciences, 1992, vol. 81, p.

871-874, and Schchipunov et al., Colloid Journal, 1995, vol. 57, p. 556-560). These emulsions have a lamellar phase and are in the form of gels even in the absence of gelling agents, hence the name organogels, which denotes this type of emulsion irrespective of the orientation of the emulsion (Water-in-Oil or Oil-in-Water).

The types of gel materials used in the present invention include polysaccharides, including but not be limited to, amylose, amylopectin, glycogen, cellulose, hyaluronate, chondroitin, heparin, dextrin, inulin, mannan, chitin, galactose, guar gum, carrageenan, agar, furcellaran, xanthan gum, other hydrocolloid gums, pectin, locust bean gum, acacia, ghatti gum, pentosan, arabinogalactan, synthetic derivatives thereof, and mixtures thereof.

Examples of materials which can form hydrogels include natural and synthetic polysaccharides and other natural and synthetic polymers and their derivatives, and combinations of these. Suitable polysaccharides and polymers include but are not limited to: amylose, amylopectin, glycogen, cellulose, hyaluronic acid, chondroitin sulfate, heparin, dextrin, inulin, mannan, chitin, galactose, guar gum, carrageenan, agar, furcellaran, xanthan gum, other hydrocolloid gums, pectic acid and pectin, locust bean gum, acacia, ghatti gum, pentosan, arabinogalactan, alginates and alginate derivatives, gellan, gellan gum, glucose, collagen (and gelatin), cellulose, carboxymethylcellulose, hydroxymethylcellulose, hydroxypropylmethylcellulose, methylcellulose, and methoxycellulose, fibrin, xanthan and xanthan gum, agarose, chitosan (polycationic polysaccharide polymers), albumin, human gamma globulin, pullulan, carrageenan (polyanionic polysaccharide polymers), dextrin, dextran, dextran sulfate, keratin, inulin, dextrose, amylose, glycogen, amylopectin, polylysine and other polyamino acids, polyesters such as polyhydroxybutyrate and polyphosphazines, poly(vinyl alcohols), poly(alkylene oxides) particularly poly(ethylene oxides), polyethylene glycol (including PEO-PPO-PEO and the like block copolymers like Pluronics®, poly(allylamines) (PAM), poly(acrylates), modified styrene polymers, pluronic polyols, polyoxamers, polypropylenes, polyurethanes, poly(uronic acids), polyvinyl chloride, poly(vinylpyrrolidone) and copolymers, graft copolymers, synthetic derivatives, blends and other mixtures of the above. Polysaccharides are the preferred polymers for this invention. Alginate, for example, is biocompatible, non-cytotoxic, non-carcinogenic, non-inflammatory, and non-immunogenic, and, therefore, a good candidate for use.

F. Types of Polymeric Materials

Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthan gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin.

Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, polyethylenes (such as, for example, polyethylene glycol (including the class of compounds referred to as Pluronics®, commercially available from BASF, Parsippany, N.J.), polyoxyethylene, and polyethylene terephthlate), polypropylenes (such as, for example, polypropylene glycol), polyurethanes, polyvinyl alcohol (PVA), polyvinyl chloride and polyvinylpyrrolidone, polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof.

The polymeric materials are selected from those materials which can be polymerized or their viscosity altered in vivo by application of exogenous means, for example, by application of light, ultrasound, radiation, or chelation, alone or in the presence of added catalyst, or by endogenous means, for example, a change to physiological pH, diffusion of calcium ions (alginate) or borate ions (polyvinyl alcohol) into the polymer, or change in temperature to body temperature (37EC).

G. Agents that Promote Angiogenesis

One class of therapeutic agents to be encapsulated by the polymer fibers of the present invention are therapeutic agents that promote angiogenesis. The successful engineering of new tissue requires the establishment of a vascular network. The induction of angiogenesis is mediated by a variety of factors, any of which may be used in conjunction with the present invention (Folkman and Klagsbrun, 1987, and references cited therein, each incorporated herein in their entirety by reference). Examples of angiogenic factors includes, but is not limited to: vascular endothelial growth factor (VEGF) or vascular permeability factor (VPF); members of the fibroblast growth factor family, including acidic fibroblast growth factor (aFGF) and basic fibroblast growth factor (bFGF); interleukin-8 (IL-8); epidermal growth factor (EGF); platelet-derived growth factor (PDGF) or platelet-derived endothelial cell growth factor (PD-ECGF); transforming growth factors alpha and beta (TGF-α, TGF-β); tumor necrosis factor alpha (TNF-α); hepatocyte growth factor (HGF); granulocyte-macrophage colony stimulating factor (GM-CSF); insulin growth factor-1 (IGF-1); angiogenin; angiotropin; angiotensin; fibrin and nicotinamide (Folkman, 1986, 1995; Auerbach and Auerbach, 1994; Fidler and Ellis, 1994; Folkman and Klagsbrun, 1987; Nagy et al., 1995).

H. Cytokines

In certain embodiments the use of particular cytokines incorporated in the polymer fibers of the present invention is contemplated. Table 2 below is an exemplary, but not limiting, list of cytokines and related factors contemplated for use in the present invention.

TABLE 2

| Cytokine | Reference |
| --- | --- |
| Human IL-1 | March et al., Nature, 315: 641, 1985 |
| Murine IL-1 | Lomedico et al., Nature, 312: 458, 1984 |
| Human IL-1 | March et al., Nature, 315: 641, 1985; Auron et al., Proc. Natl. Acad. Sci. USA, 81: 7907, 1984 |
| Murine IL-1 | Gray, J Immunol., 137: 3644, 1986; Telford, NAR, 14: 9955, 1986 |
| Human IL-Ira | Eisenberg et al., Nature, 343: 341, 1990 |
| Human IL-2 | Taniguchi et al., Nature, 302: 305, 1983; Maeda et al., Biochem. Biophys. Res. Commun., 115: 1040, 1983 |
| Human IL-2 | Taniguchi et al., Nature, 302: 305, 1983 |
| Human IL-3 | Yang et al., Cell, 47: 3, 1986 |
| Murine IL-3 | Yomkota et al., Proc. Natl. Acad. Sci. USA, 81: 1070, 1984; Fung et al., Nature, 307: 233, 1984; Miyatake et al., Proc. Natl. Acad. Sci. USA, 82: 316, 1985 |
| Human IL-4 | Yomkota et al., Proc. Natl. Acad. Sci. USA, 83: 5894, 1986 |
| Murine IL-4 | Norman et al., Nature, 319: 640, 1986; Lee et al., Proc. Natl. Acad. Sci. USA, 83: 2061, 1986 |
| Human IL-5 | Azuma et al., Nuc. Acids Res., 14: 9149, 1986 |
| Murine IL-5 | Kinashi et al., Nature, 324: 70, 1986; Mizuta et al., Growth Factors, 1: 51, 1988 |
| Human IL-6 | Hirano et al., Nature, 324: 73, 1986 |
| Murine IL-6 | Van Snick et al., Eur. J. Immunol., 18: 193, 1988 |
| Human IL-7 | Goodwin et al., Proc. Natl. Acad. Sci. USA, 86: 302, 1989 |
| Murine IL-7 | Namen et al., Nature, 333: 571, 1988 |
| Human IL-8 | Schmid et al., J. Immunol., 139: 250, 1987; Matsushima et al., J. Exp. Med., 167: 1883, 1988; Lindley et al., Proc. Natl. Acad. Sci. USA, 85: 9199, 1988 |
| Human IL-9 | Renauld et al., J. Immunol., 144: 4235, 1990 |
| Murine IL-9 | Renauld et al., J. Immunol., 144: 4235, 1990 |
| Human Angiogenin | Kurachi et al., Biochemistry, 24: 5494, 1985 |
| Human GRO | Richmond et al., EMBO J., 7: 2025, 1988 |
| Murine MIP-1 | Davatelis et al., J. Exp. Med., 167: 1939, 1988 |
| Murine MIP-1 | Sherry et al., J. Exp. Med., 168: 251, 1988 |
| Human MIF | Weiser et al., Proc. Natl. Acad. Sci. USA, 86: 7522, 1989 |
| Human G-CSF | Nagata et a l., Nature, 319: 415, 1986; Souza et al., Science, 232: 61, 1986 |
| Human GM-CSF | Cantrell et al., Proc. Natl. Acad. Sci. USA, 82: 6250, 1985; Lee et al., Proc. Natl. Acad. Sci. USA, 82: 4360, 1985; Wong et al., Science, 228: 810, 1985 |
| Murine GM-CSF | Gough et al., EMBO J., 4: 645, 1985 |
| Human M-CSF | Wong, Science, 235: 1504, 1987; Kawasaki, Science, 230; 291, 1985; Ladner, EMBO J., 6: 2693, 1987 |
| Human EGF | Smith et al., Nuc. Acids Res., 10: 4467, 1982; Bell et al., NAR, 14: 8427, 1986 |
| Human TGF- | Derynck et al., Cell, 38: 287, 1984 |
| Human FGF Acidic | Jaye et al., Science, 233: 541, 1986; Gimenez-Gallego et al., Biochem. Biophys. Res. Commun. 138: 611, 1986; Harper et al., Biochem., 25: 4097, 1986 |
| Human-ECGF | Jaye et al., Science, 233: 541, 1986 |
| Human FGF basic | Abraham et al., EMBO J., 5: 2523, 1986; Sommer et al., Biochem. Biophys. Res. Comm., 144: 543, 1987 |
| Murine IFN- | Higashi et al., J. Biol. Chem., 258: 9522, 1983; Kuga, NAR, 17: 3291, 1989 |
| Human IFN- | Gray et al., Nature, 295: 503, 1982; Devos et al., NAR, 10: 2487, 1982; Rinderknecht, J. Biol. Chem., 259: 6790, 1984 |
| Human IGF-I | Jansen et al., Nature, 306: 609, 1983; Rotwein et al., J. Biol. Chem., 261: 4828, 1986 |
| Human IGF-II | Bell et al., Nature, 310: 775, 1984 |
| Human-NGF chain | Ullrich et al., Nature, 303: 821, 1983 |
| Human NT-3 | Huang EJ. Et al., Development. 126 (10): 2191–203, 1999 May. |
| Human PDGF A chain | Betsholtz et al., Nature, 320: 695, 1986 |
| Human PDGF B chain | Johnsson et al., EMBO J., 3: 921, 1984; Collins et al., Nature, 316: 748, 1985 |
| Human TGF-1 | Derynck et al., Nature, 316: 701, 1985 |
| Human TNF- | Pennica et al., Nature, 312: 724, 1984; Fransen et al., Nuc. Acids Res., 13: 4417, 1985 |
| Human TNF- | Gray et al., Nature, 312: 721, 1984 |
| Murine TNF- | Gray et l., Nucl. Acids Res., 15: 3937, 1987 |

TABLE 2-continued

| Cytokine | Reference |
|---|---|
| Human E-Selectin | Bevliacqua et al., Science, 243: 1160, 1989; Hensley et al., J. Biol. Chem., 269: 23949, 1994 |
| Human ICAM-1 | Simmons et al., Nature, 331: 624, 1988 |
| Human PECAM | Simmons et al., J. Exp. Med., 171: 2147, 1990 |
| Human VCAM-1 | Hession et al., J. Biol. Chem., 266: 6682; Osborn et al., Cell, 59: 1203, 1989 |
| Human L-Selectin (membrane bound) | Ord et al., J. Biol. Chem., 265: 7760, 1990; Tedder et al., J. Exp. Med., 170: 123, 1989 |
| Human L-Selectin (soluble form) | Ord et al., J. Biol. Chem., 265: 7760, 1990; Tedder et al., J. Exp. Med., 170: 123, 1989 |
| Human Calcitonin | Le Moullec et al., FEBS Lett., 167: 93, 1984 |
| Human Hirudin (E. coli optimized) | Dodt et al., FEBS Lett., 165: 180, 1984 |

I. Polynucleotides

The polynucleotides to be incorporated within the polymer fibers of the present invention extend to the full variety of nucleic acid molecules. The nucleic acids thus include genomic DNA, cDNAs, single stranded DNA, double stranded DNA, triple stranded DNA, oligonucleotides, Z-DNA, mRNA, tRNA and other RNAs. DNA molecules are generally preferred, even where the DNA is used to express a therapeutic RNA, such as a ribozyme or antisense RNA.

A "gene" or DNA segment encoding a selected protein or RNA, generally refers to 10 a DNA segment that contains sequences encoding the selected protein or RNA, but is isolated away from, or purified free from, total genomic DNA of the species from which the DNA is obtained. Included within the terms "gene" and "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

The present invention does not require that highly purified DNA or vectors be is used, so long as any coding segment employed encodes a selected protein or RNA and does not include any coding or regulatory sequences that would have a significant adverse effect on the target cells. Therefore, it will also be understood that useful nucleic acid sequences may include additional residues, such as additional non-coding sequences flanking either of the 5' or 3' portions of the coding region or may include various internal sequences, i.e., introns, that are known to occur within genes.

Many suitable DNA segments may be obtained from existing, including commercial sources. One may also obtain a new DNA segment encoding a protein of interest using any one or more of a variety of molecular biological techniques generally known to those skilled in the art. For example, cDNA or genomic libraries may be screened using primers or probes with designed sequences. Polymerase chain reaction (PCR) may also be used to generate a DNA fragment encoding a protein of interest.

After identifying an appropriate selected gene or DNA molecule, it may be inserted into any one of the many vectors currently known in the art, so that it will direct the expression and production of the selected protein when incorporated into a target cell. In a recombinant expression vector, the coding portion of the DNA segment is positioned under the control of a promoter/enhancer element. The promoter may be in the form of the promoter that is naturally associated with a selected gene, as may be obtained by isolating the 5' non-coding sequences located upstream of the coding segment or exon, for example, using recombinant cloning and/or PCR technology.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a selected gene in its natural environment. Such promoters may include those normally associated with other selected genes, and/or promoters isolated from any other bacterial, viral, eukaryotic, or mammalian cell. Naturally, it will be important to employ a promoter that effectively directs the expression of the DNA segment in the chosen target cells.

The use of recombinant promoters to achieve protein expression is generally known to those of skill in the art of molecular biology, for example, see Sambrook et al. (1989; incorporated herein by reference). The promoters employed may be constitutive, or is inducible, and can be used under the appropriate conditions to direct high level or regulated expression of the introduced DNA segment. Expression of genes under the control of constitutive promoters does not require the presence of a specific substrate to induce gene expression and will occur under all conditions of cell growth. In contrast, expression of genes controlled by inducible promoters is responsive to the presence or absence of an inducing agent.

Promoters isolated from the genome of viruses that grow in mammalian cells, e.g., RSV, vaccinia virus 7.5K, SV40, HSV, adenoviruses MLP, MMTV LTR and CMV promoters, may be used herewith, as well as promoters produced by recombinant DNA or synthetic techniques. Currently preferred promoters are those such as CMV, RSV LTR, the SV40 promoter alone, and the SV40 promoter in combination with the SV40 enhancer.

Exemplary tissue specific promoter/enhancer elements and transcriptional control regions that exhibit tissue specificity include, but are not limited to: the elastase I gene control region that is active in pancreatic acinar cells; the insulin gene control region that is active in pancreatic cells; the immunoglobulin gene control region that is active in lymphoid cells; the albumin, 1-antitrypsin and -fetoprotein gene control regions that are active in liver; the -globin gene control region that is active in myeloid cells; the myelin basic protein gene control region that is active in oligodendrocyte cells in the brain; the myosin light chain-2 gene control region that is active in skeletal muscle; and the gonadotropic releasing hormone gene control region that is active in the hypothalamus.

Specific initiation signals may also be required for sufficient translation of inserted protein coding sequences. These signals include the ATG initiation codon and adjacent sequences. In cases where the entire coding sequence, including the initiation codon and adjacent sequences are inserted into the appropriate expression vectors, no additional translational control signals may be needed. However, in cases where only a portion of the coding sequence is inserted, exogenous translational control signals, including the ATG initiation codon should be provided. The initiation codon must be in phase with the reading frame of the protein coding sequences to ensure translation of the entire insert. These exogenous translational control signals and initiation codons can be of a variety of origins, both natural and synthetic. The efficiency and control of expression may be enhanced by the inclusion of transcription attenuation sequences, enhancer elements, etc.

A variety of vectors may be used including, but not limited to, those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include gtl0, gtl 1, gtl8-23, ZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Vectors that allow for the in vitro transcription of RNA, such as SP6 vectors, may also be used to produce large quantities of RNA that may be incorporated into matrices.

The selected genes and DNA segments may also be in the form of a DNA insert located within the genome of a recombinant virus, such as, for example a recombinant herpes virus, retroviruses, vaccinia viruses, adenoviruses, adeno-associated viruses or bovine papilloma virus. While integrating vectors may be used, non-integrating systems, which do not transmit the gene product to daughter cells for many generations will often be preferred. In this way, the gene product is expressed during a defined biological process, e.g., a wound healing process, and as the gene is diluted out in progeny generations, the amount of expressed gene product is diminished.

In such embodiments, to place the gene in contact with a target cell, one would prepare the recombinant viral particles, the genome of which includes the gene insert, and contact the target cells or tissues via release from the polymer fiber of the present invention, whereby the virus infects the cells and transfers the genetic material.

Genes with sequences that vary from those described in the literature are also contemplated for use in the invention, so long as the altered or modified gene still encodes a protein that functions to effect the target cells in the desired (direct or indirect) manner. These sequences include those caused by point mutations, those due to the degeneracies of the genetic code or naturally occurring allelic variants, and further modifications that have been introduced by genetic engineering, i.e., by the hand of man.

Techniques for introducing changes in nucleotide sequences that are designed to alter the functional properties of the encoded proteins or polypeptides are well known in the art. Such modifications include the deletion, insertion or substitution of bases, and thus, changes in the amino acid sequence. Changes may be made to increase the activity of a protein, to increase its biological stability or half-life, to change its glycosylation pattern, confer temperature sensitivity or to alter the expression pattern of the protein, and the like. All such modifications to the nucleotide sequences are encompassed by this invention.

It is an advantage of the present invention that one or more than one selected gene may be used in the gene transfer methods and compositions. The nucleic acid delivery methods may thus entail the administration of one, two, three, or more, selected genes. The maximum number of genes that may be applied is limited only by practical considerations, such as the effort involved in simultaneously preparing a large number of gene constructs or even the possibility of eliciting an adverse cytotoxic effect. The particular combination of genes may be chosen to alter the same, or different, biochemical pathways. For example, a growth factor gene may be combined with a hormone gene; or a first hormone and/or growth factor gene may be combined with a gene encoding a cell surface receptor capable of interacting with the polypeptide product of the first gene.

In using multiple genes, they may be combined on a single genetic construct under control of one or more promoters, or they may be prepared as separate constructs of the same of different types. Thus, an almost endless combination of different genes and genetic constructs may be employed. Certain gene combinations may be designed to, or their use may otherwise result in, achieving synergistic effects on cell stimulation and tissue growth, any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic segment or gene could be administered in combination with further agents, such as, e.g. proteins or polypeptides or various pharmaceutically active agents. So long as genetic material forms part of the composition, there is virtually no limit to other components which may also be included, given that the additional agents do not cause a significant adverse effect upon contact with the target cells or tissues. The nucleic acids may thus be delivered along with various other agents, for example, in certain embodiments one may wish to administer an angiogenic factor as disclosed in U.S. Pat. No. 5,270,300 and incorporated herein by reference.

As the chemical nature of genes, i.e., as a string of nucleotides, is essentially invariant, and as the process of gene transfer and expression are fundamentally the same, it will be understood that the type of genes transferred by the fiber matrices of the present invention is virtually limitless. This extends from the transfer of a mixture of genetic material expressing antigenic or immunogenic fragments for use in DNA vaccination; to the stimulation of cell function, as in wound-healing; to aspects of cell killing, such as in transferring tumor suppressor genes, antisense oncogenes or apoptosis-inducing genes to cancer cells.

By way of example only, genes to be supplied by the invention include, but are not limited to, those encoding and expressing: hormones, growth factors, growth factor receptors, interferons, interleukins, chemokines, cytokines, colony stimulating factors and chemotactic factors; transcription and elongation factors, cell cycle control proteins, including kinases and phosphatases, DNA repair proteins, apoptosis-inducing genes; apoptosis-inhibiting genes, oncogenes, antisense oncogenes, tumor suppressor genes; angiogenic and anti-angiogenic proteins; immune response stimulating and modulating proteins; cell surface receptors, accessory signaling molecules and transport proteins; enzymes; and anti-bacterial and anti-viral proteins.

J. Kits

All the essential materials and reagents required for the various aspects of the present invention may be assembled together in a kit. The kits of the present invention also will typically include a means for containing the vials comprising the desired components in close confinement for commercial sale such as, e.g., injection or blow-molded plastic containers into which the desired vials are retained. Irrespective of the number or type of containers, the kits of the invention are typically packaged with instructions for use of the kit components.

WORKING EXAMPLES

The following examples are included to demonstrate preferred embodiments of the invention and are not intended to limit the scope of the invention in any way. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

3.2. Extrusion of Gel or Hydrogel Bored Fibers

Figure 7:
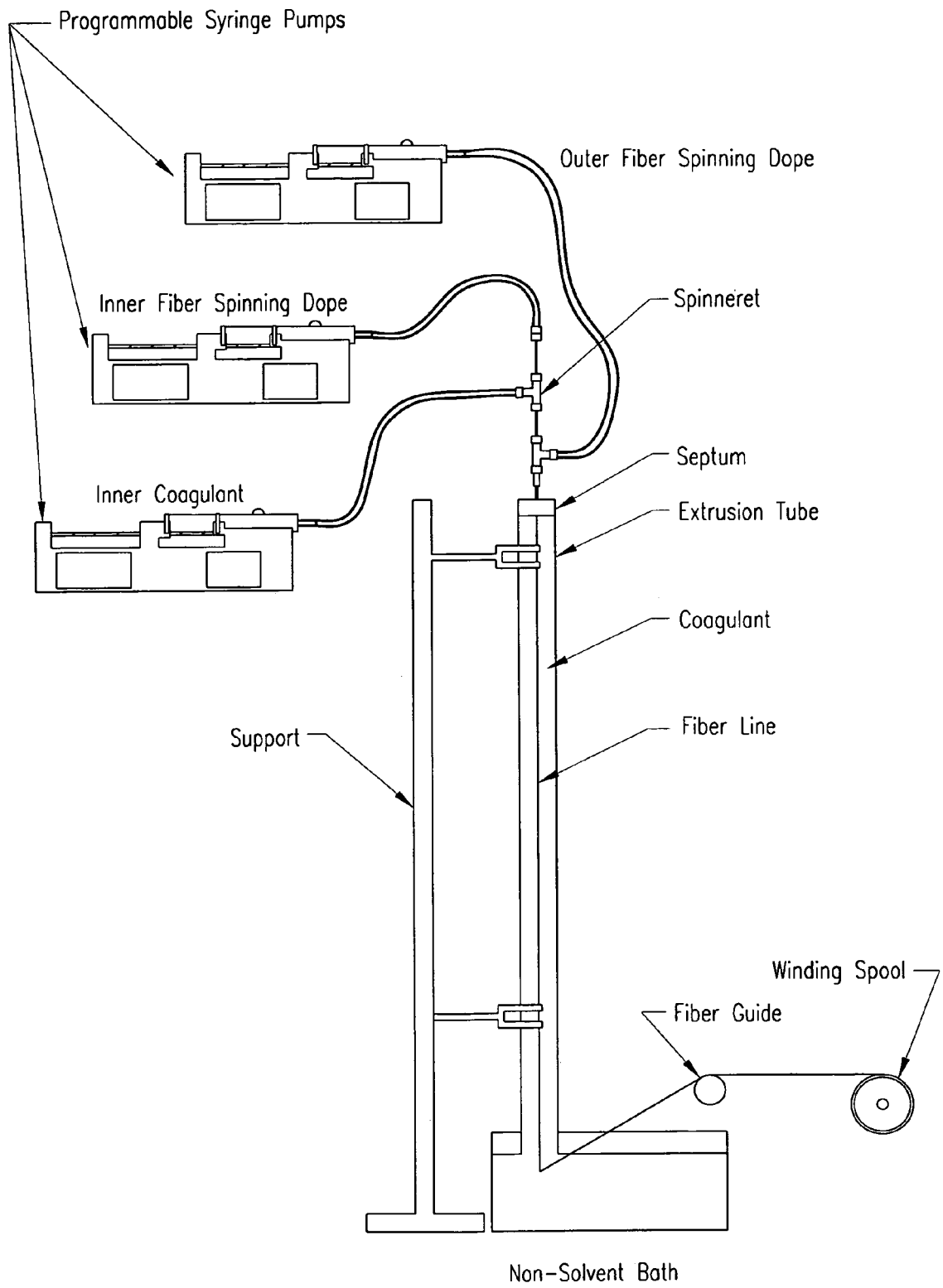
FIG. 7 depicts a wet extrusion apparatus used to extrude fibers of the invention.

In one embodiment of the present invention, the following procedure is used to create gel or hydrogel bored drug-releasing fibers. The apparatus used is depicted in FIG. 7, which details a fiber spinneret in which a coagulant bore fluid is fed through a small diameter hypodermic tube, which is centered in a blunt-end hypodermic needle. However, any similar configuration including scaled-up versions and specifically built apparatus' are included within the scope of the invention. This configuration allows for an annulus of polymer to flow through the spinneret, bored by a water-based gel or hydrogel. First, a biodegradable polymer such as poly(L-lactic acid) (PLLA), poly(DL-lactic acid), polycaprolactone, poly(glycolic acid), polyanhydride, or copolymers or blends of these or other biodegradable polymers is dissolved in some appropriate solvent (A) at concentrations ranging from 5 to 30 wt % depending on the type of polymer, 10 wt % being preferred for PLLA at 200 kD molecular weight. In this embodiment, solvent (A) has low miscibility with water, and is very miscible with the coagulation bath solvent (B), but not with the water in the gel or hydrogel in the bore. The water does not function as a solvent or non-solvent in this application. Preferred choices of solvent (A) include chloroform and methylene chloride. Once the polymer is dissolved in the chosen solvent, a non-solvent (solvent C) is typically added to the polymer solution in an appropriate concentration to reduce the solvation power of the solvent system, yet not bring the solution to its cloud point. This non-solvent is highly miscible with solvent (A), and with solvent (B), and in some cases may be the same as solvent (B). Typical choices include iso-octane, cyclohexane, and hexane. This non-solvent brings the polymer in the solution close to its cloud point, so that the solution will more quickly precipitate to form a fiber when extruded into the coagulant bath, solvent (B).

The gel or hydrogel is prepared using standard procedures known to those who practice the art. As an example, for an internally gelled alginate bore fluid, sodium alginate powder is first dissolved in distilled-deionized water to yield a concentration in the range of 0.5 to 50 wt %, with 1 wt % being desired for this example. Once dissolved, the solution is sterile filtered to provide an appropriate stock for the gel extrusion process. To promote internal gelation of the alginate, an appropriate quantity of calcium carbonate, $CaCO_3$, is added to the solution and mixed thoroughly by vortexing, sonicating, or homogenizing. Calcium carbonate is not soluble in water at neutral pH, so the powder ultimately is suspended in the alginate solution. To this solution, an appropriate quantity of D-Glucono-delta-Lactone (GDL) is added to slowly drop the solution pH, which initiates liberation of free $Ca^{++}$ from the $CaCO_3$ to cross-link the guluronic acid residues in the alginate, thus forming a hydrogel. The rate of gelation and the properties of the gel can be controlled through the concentration of $CaCO_3$ and the ration of GDL to $CaCO_3$ used in the solution.

Figure 8:
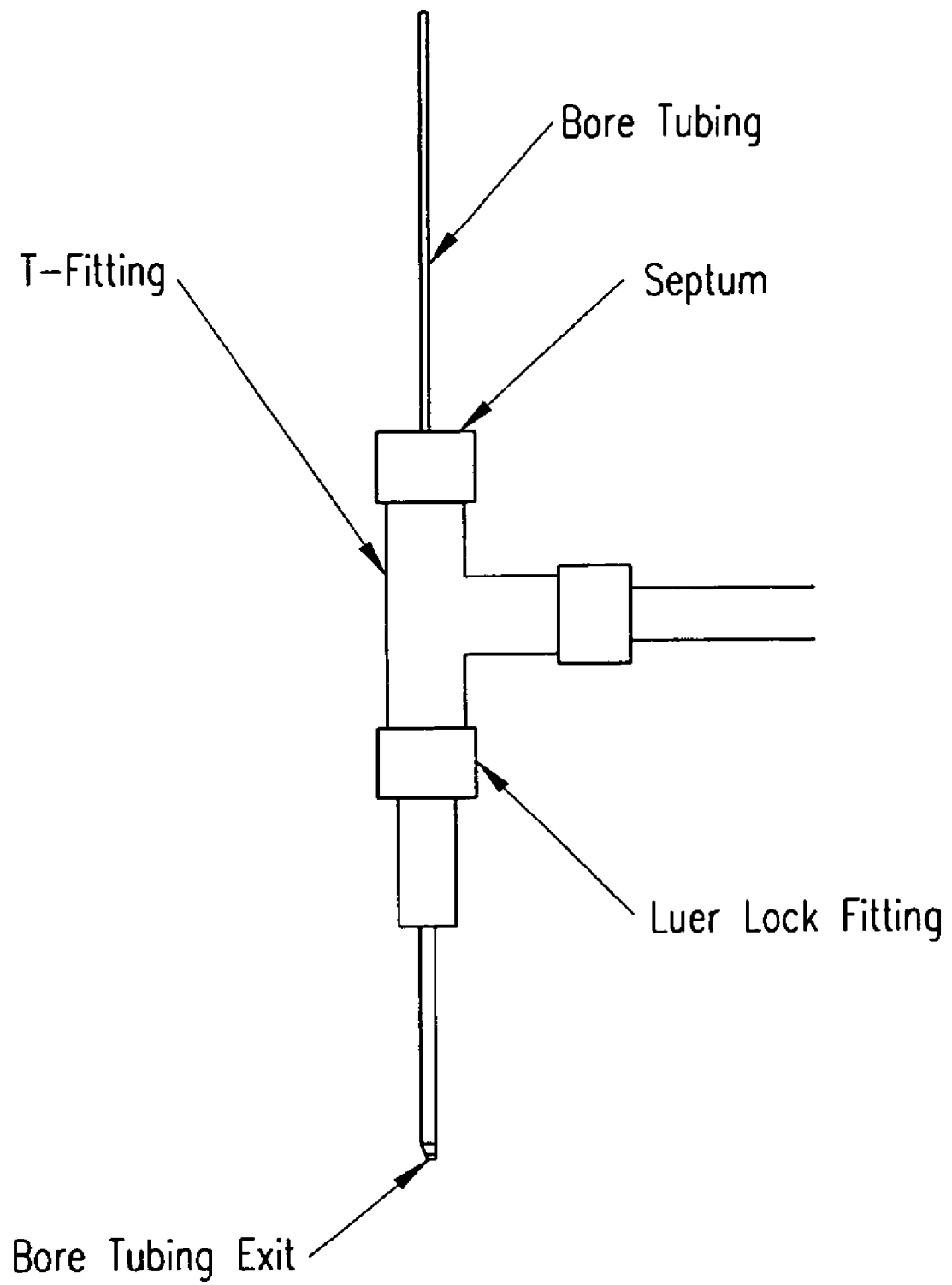
FIG. 8 depicts a spinneret used in the present invention.
Figure 9:
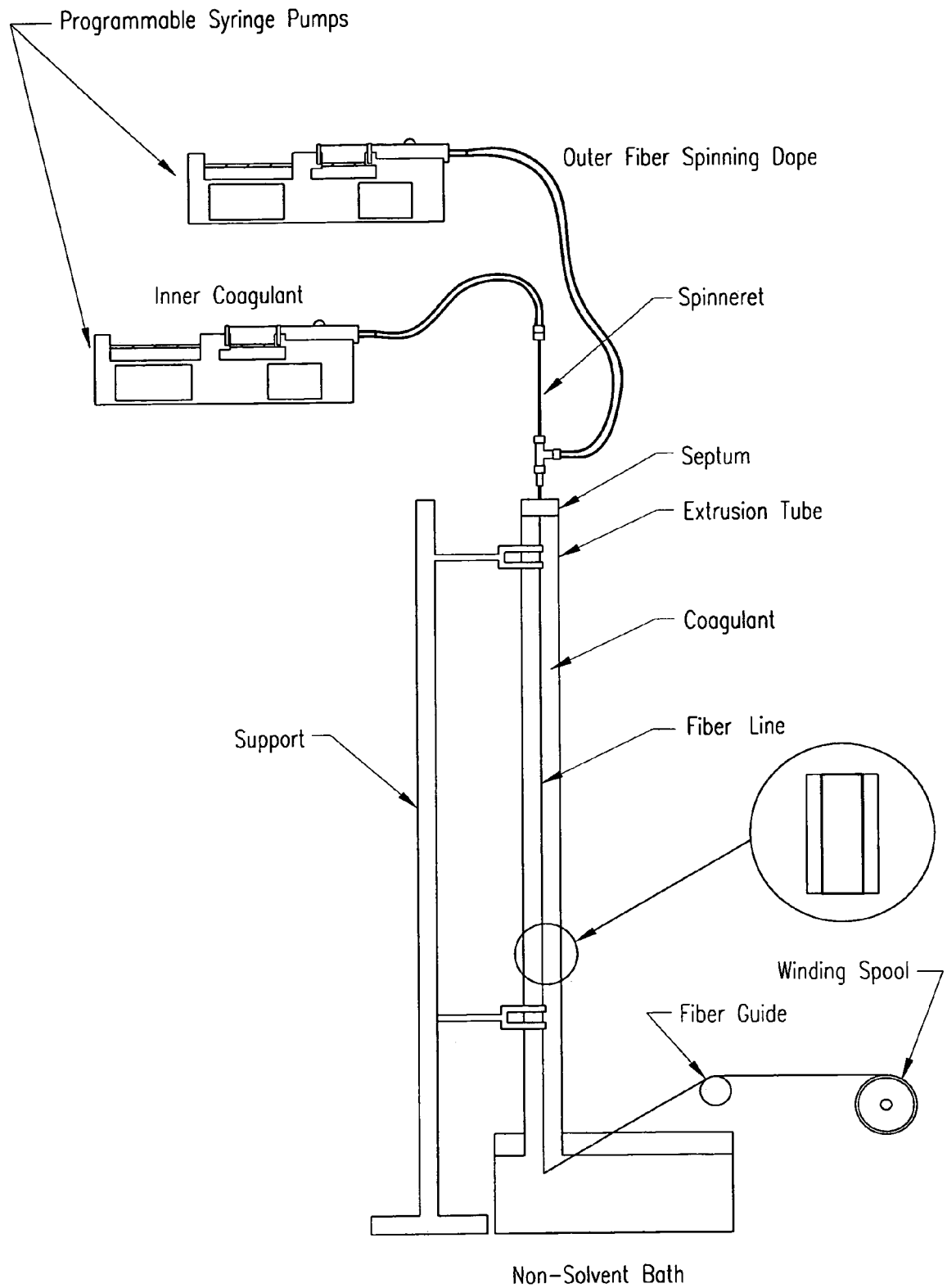
FIG. 9 depicts a triple apparatus used in the extrusion of fibers of the invention.
Figure 10:
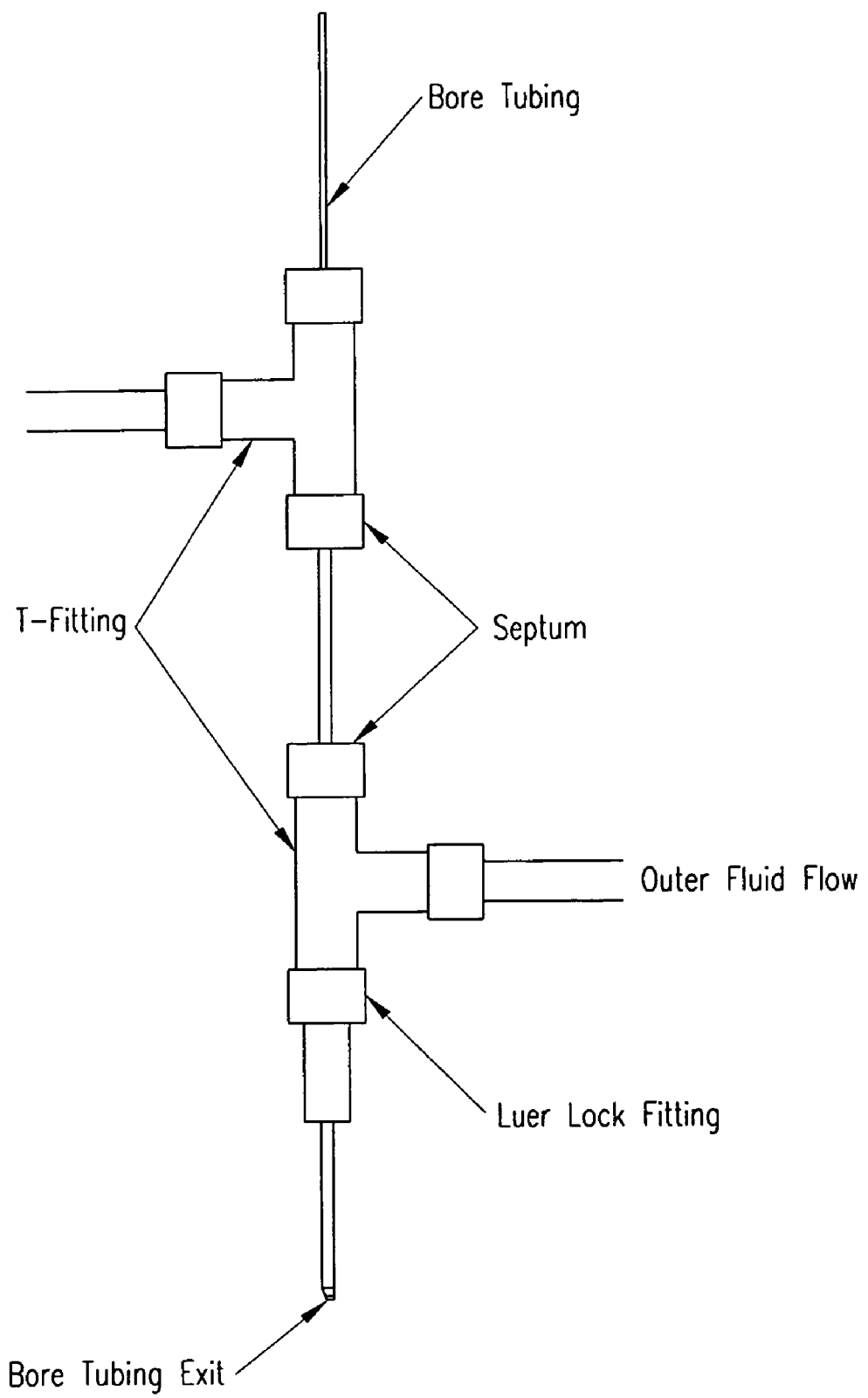
FIG. 10 depicts a triple spinneret used in the manufacture of multicomponent fibers.
Figure 11:
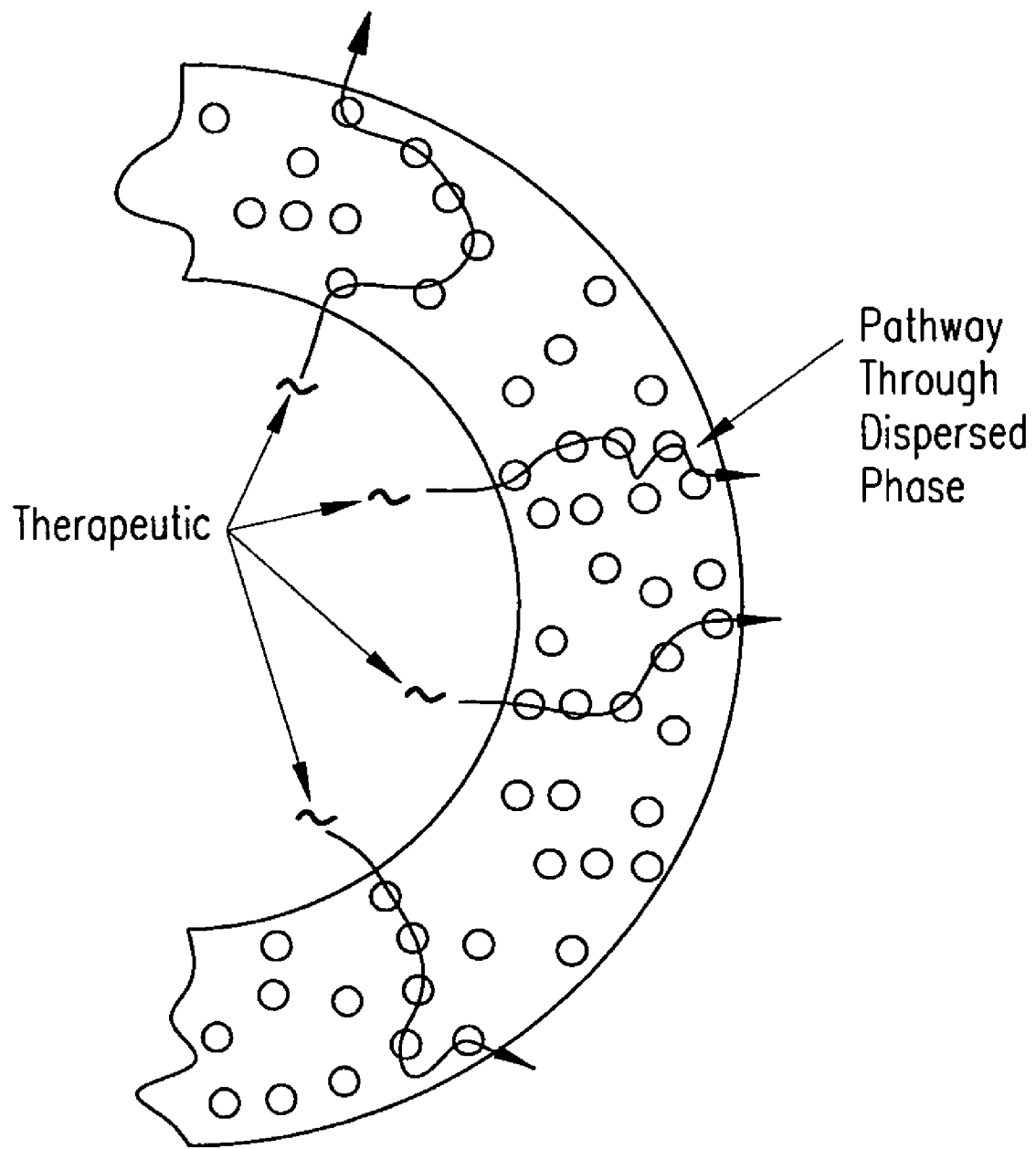
FIG. 11 depicts the flow of a therapeutic through the walls of an emulsion-loaded fiber.

The prepared gel solution and the polymer solution are then immediately extruded into the coagulating bath containing solvent (B), through the spinneret device depicted in FIG. 8, such that the polymer flows around a center tube containing the gel or hydrogel and, if desired, a drug of choice either dissolved in the gel, or encapsulated in nanospheres or liposomes and suspended in the gel. The polymer solution and gel or hydrogel core are extruded into the coagulation bath through a spinneret according to the size of the desired fiber, as these fibers are not typically drawn, the final fiber size is close to the spinneret size. The optimum ration of outer annulus to inner gel or hydrogel diameter needs to be experimentally determined. For example, to obtain fibers whose outer diameter are approximately 500 Elm, the inventor's laboratory has used an outer lumen of 18 gage with a 24 or 25 gage inner lumen for the bore fluid. Any water-based gel, precursor hydrogel component, or hydrogel can be delivered through the center tube. Frequently, the inner gel or hydrogel is carrying a drug that is incompatible with organic solvents, or the gel or hydrogel does not tolerate the presence of organic solvents. Therefore, it is generally preferred that the solvent for the gel or hydrogel (generally water) is immiscible with solvents (A), (B) and (C). Solvent (B) must be highly miscible with solvents (A) and (C), immiscible with the water component of the bore fluid, and must be a non-solvent for the polymer; hexane and pentane are the most typical choices, but any solvent that meets the above criteria and quickly draws the solvent from the polymer solution will theoretically work. Wherefore, chloroform and pentane make a good solvent and coagulating bath combination with iso-octane as the added non-solvent. Because solvent (A) is highly miscible with coagulating bath solvent (B), it freely diffuses from the polymer solution stream into the coagulating bath, reducing the solvent power of the polymer solution below the cloud point, which causes the polymer to begin to precipitate to form a solid polymer sheath. Occasionally, the polymer sheath must begin to precipitate and form before it is subjected to the stress of being exposed to the gel or hydrogel flowing in the inner lumen. This requires that the axial positions of the inner lumen protrude below the outlet of the outer annulus (0-2 mm typical in inventor's laboratory) to ensure that the polymer solution is exposed to the coagulant bath just prior to the gel or hydrogel bore fluid contacting the polymer. The non-solvent (C), incorporated into the polymer solution accelerates the precipitation process. As neither solvent (A) nor (B) freely diffuse into the bore fluid, only a single coagulant front is created as the polymer exits the spinneret, thereby encapsulating the bore gel or hydrogel. The distance the fiber drops into the coagulating bath is important to the formation of the fiber and its ultimate properties, and is typically 10-30 cm. In the inventor's laboratory, the fiber has been allowed to freely fall and collect at the bottom of the coagulating bath container; however, other designs including drawing the fiber out of the coagulating bath are included as part of this invention. The extruded fiber may be post-processed and stored in a number of ways including freeze-dried, frozen, or oven dried and placed in a desecrator or freezer, depending upon recommended storage conditions of the loaded biomolecules and the properties of the gel or hydrogel.

Example 2

3.3. Extrusion of Gel Coated Polymer Fiber

In another embodiment of the present invention, a PLLA or other biodegradable polymer fiber coated with a hydrogel is created. The extrusion process is similar to that described, except the coagulant bath used contains a coagulant or crosslinker for the hydrogel. The polymer and hydrogel are extruded through a spinneret similar to that previously described, with the polymer solution (possibly containing a drug in a dispersed aqueous or gel phase) extruded through the inner bore of the spinneret and the gel or hydrogel (possibly containing a drug) solution extruded through the outer annulus of the spinneret. The solutions are prepared as described or as otherwise known to those who practice the art, and are extruded at the same time through the spinneret. In the case of a dual lumen spinneret, the polymer solution is extruded without direct exposure to a coagulant. In this case, the polymer solvent must be removed by a post-processing step, or if there are no reasons to the contrary, the coagulating bath may contain a mixture of solvents, at least one of which miscible with both water and the polymer solvent; examples of which include isopropyl alcohol, acetone etc. This will allow the polymer solvent (typically chloroform or methylene chloride) to leave through the gel or hydrogel exterior layer being carried by the water miscible solvent. The coagulant bath also contains a solution known to those who practice the art that crosslinks or otherwise forms the gel or hydrogel. In the case of alginate hydrogel, the coagulant bath can be an appropriate concentration solution of CaCl2 in water. As the polymer solution, and alginate solution flow from the spinneret, the alginate solution (which could contain CaCO3 and GDL as noted above) contacts the coagulant and is crosslinked by calcium ions in the solution. If a polymer coagulant is used, solvent in the polymer/emulsion will diffuse into the coagulant and the polymer will form a fiber. If no coagulant is used, the polymer solution will be encapsulated by the rapidly crosslinking alginate solution such that an alginate shelled fiber will form. The residual solvent within the polymer can be removed by appropriate post-processing techniques.

Example 3

Extrusion of Gel or Hydrogel Exterior Hollow Fibers Using a Coagulant Bore Fluid In one embodiment of the present invention, the following procedure is used to create gel or hydrogel exterior, hollow fibers. The apparatus includes a triple lumen spinneret, which also implies three pumps. The coagulant bath consists of a glass tube mounted vertically with one end immersed into reservoir of coagulant bath consists of a glass tube mounted vertically with one end immersed into a reservoir of coagulant fluid, and the other end sealed with a septum. Coagulant is drawn into the tube from the reservoir by piercing the septum with a needle and extracting the air in the tube with a large volume syringe. When filled, the syringe needle is removed and the septum seals the tube. As in example 2, the coagulant must include a means of gelling the exterior layer of gel or hydrogel. Again, in the case of alginate for example, a solution of calcium chloride may be appropriate. The gel or hydrogel solution flows through the outermost lumen, the biodegradable polymer through the inner lumen, and a coagulant for the polymer as defined above, flows through the innermost lumen. The fiber is drawn from the coagulation bath at a determined rate. In the laboratory, the inventors have used a cylinder attached to a modified variable-speed lathe that can accurately maintain its angular velocity. The drawn and extruded fiber is then removed from the cylinder and coagulant in the center of the fiber without collapsing the fiber. Residual coagulant and water are removed by freeze-drying, freezing or oven drying the fiber and placing it into a desecrator or freezer, depending upon recommended storage conditions.

Example 4

Extrusion of Hollow Fibers Using Water as a Bore Fluid (Water Bore Fiber)

In one embodiment of the present invention, the following procedure is used to create water-bored drug-released fibers. The apparatus is similar to that used in Example 1. This configuration allows for an annulus of polymer to flow through the spinneret, bored by a water-based fluid. First, a biodegradable polymer such as poly(L-lactic acid) (PLLA), poly(DL-lactic acid), polycaprolactone, poly(glycolic acid), polyanhydride, or copolymers or blends of these or other biodegradable polymers is dissolved in some appropriate solvent (A) at concentrations ranging from 5 to 30 wt % depending on the type of polymer, 10 wt % being preferred for PLLA at 200 kD molecular weight. In this embodiment, solvent (A) has low miscibility with water, and is very miscible with the coagulation bath solvent (B), but not with the water in the bore. The water does not function as a solvent or non-solvent in this application. Preferred choices of solvent (A) include chloroform and methylene chloride. Once the polymer is dissolved in the chosen solvent, a non-solvent is added to the polymer solution in an appropriate concentration to reduce the solvating power of the solvent system of the polymer, yet not bring the solution to its cloud point. This non-solvent (solvent C) is highly miscible with solvent (A), and with solvent (B). Typical choices include iso-octane, cyclohexane, and hexane. This nonsolvent brings the polymer in the solution close to its point of coagulation, so that the solution will more quickly form a fiber when extruded into the coagulant bath.

The polymer solution is then extruded into a coagulating bath containing solvent (B), though a spinneret device such that the polymer flows around a center tube containing water and, if desired, a drug of choice either dissolved in the water, or encapsulated in nanospheres or liposomes and suspended in the water. The polymer solution is extruded into the coagulation bath through a dispensing tip ranging in size from 16 gage down to 27 gage, with the hypodermic tubing containing the water bore fluid appropriately sized to fit within the chosen dispensing tip. Any water-based fluid can be delivered through the center tube, provided this solution is immiscible with solvent (A). Solvent (B) must be highly miscible with solvents (A) and (C), and must be a non-solvent for the polymer; hexane and pentane are the most typical choices, but any solvent that is a non-solvent for the polymer and highly miscible with solvents (A) and (C) will work for this application, provided it quickly draws the solvent from the polymer solution. For example pentane is very miscible with chloroform and iso-octane, yet is a non-solvent for the polymer. Therefore, chloroform, iso-octane and pentane make a good solvent, non-solvent, and coagulating bath combination. Because solvent (A) is highly miscible with coagulating bath solvent (B), it freely diffuses from the polymer solution stream into the coagulating bath. The relative axial positions of the inner hypodermic tubing and the dispensing tip are adjusted to assure the annulus of polymer solution is exposed to the coagulant bath prior to the water bore contacting the polymer. The non-solvent incorporated into the polymer solution accelerates the precipitation process, such that a shell is formed in the polymer that entraps the bore solution. Neither solvent (A) nor (C) freely diffuse into the bore fluid, so only a single coagulant front is created as the polymer exits the spinneret. Additionally, the immiscibility of the solvents with the bore protects it and its contents. The coagulant bath used for this application consists of a 250 ml or greater flask into which the fiber is allowed to drop and spool as it coagulates. The height of the drop is important to the formation of the fiber, and is typically 10-30 cm. The extruded fiber is removed from the flask and either freeze-dried, frozen, or oven dried and placed in a desecrator or freezer, depending upon recommended storage conditions.

3.4. Example 5

Alternate Fabrication Technique for Example 1, for Hydrophilic Fiber

The only difference is to use as a coagulating bath a molecule such as poly(ethylene glycol) (PEG) of low molecular weight (in the range of 200 to 600 Daltons is typical). This polymer is miscible with chloroform and methylene chloride, yet a nonsolvent for the polymer, such as PLLA. Therefore, it qualifies as a coagulation bath, however, this unique coagulating bath creates an interpenetrating network of PEG in the wall of the fiber, making them hydrophilic upon exposure to an aqueous environment. This can have interesting implications for implantation and may alter cellular response to the fibers.

Example 6

Neural Tissue Engineering

In this aspect of the present invention, parallel arrays of fibers are packed into tubes 25 and loaded with neurotrophins for axonal growth. The tube may be a very large version of a fiber of composition claimed in this invention, wherein the gel or hydrogel core may have a concentration of zero, or alternatively, be designed with an outer sheath of gel or hydrogel, with a multi-component inner core of gel or hydrogel with an intermediate layer consisting of biodegradable polymer. The innermost gel or hydrogel may have a concentration of zero, and the biodegradable polymer layer may be loaded with therapeutic agents either in a dispersed phase or directly mixed with the polymer. The exterior gel or hydrogel may also contain therapeutic agents as may the interior gel or hydrogel. Within the tube is a parallel array of fibers, whose composition may or may not be described by this invention or our prior invention. For this example, at least one component, either the tube, or at least one fiber must be of a composition as described in this invention. This array of fibers inside the tube is placed in severed peripheral or central nerves. The therapeutic agents may be loaded in a linear or some other appropriate gradient in every element of the device in which they are loaded (the exterior gel or hydrogel of the tube, the intermediate biodegradable polymer layer, or the innermost core of the tube, as well as the individual fibers within the tube in any and all possible constituents as described herein), but the gradient can differ in every occurrence within the device as desired. This device is implanted bridging the gap between the ends of the nerve stumps. As the device releases its therapeutic agents, which may consist of neurotrophins, anti-inflammatory agents, angiogenic factors, specific chemotactic or chemorepulsive agents etc., axons, vasculature, and other supporting cells and tissues begin to migrate across the lesion. Once the axons reach the distal end, guidance cues are provided by existing Schwann or glial cells and reconnections can then be made. It has been previously found that axons receive contact guidance by these fiber bundles and are able to traverse at least 1.8 cm in a rat sciatic nerve resection using non-loaded fibers. The optimal density of unloaded fibers in the tube is approximately 32 fibers in a 1.5 mm diameter tube for rat sciatic nerve growth.

Example 7

Preparation and Use of Polymer Fiber Stents

In another embodiment, fibers can be loaded with a drug of interest and used in stents or other medical devices where mechanical strength is required. The stents can be woven in such a manner as to have loaded fibers intermingled with unloaded fibers if needed for mechanical properties.

Fibers can also be used in conjunction with commercially available stents to deliver drugs at the placement site. In this case, the fibers would not provide any mechanical support, but would only serve as a drug delivery reservoir.

Example 8

Preparation and Use of Wound Dressings

In another embodiment, a gauze or dressing can be made from these fibers. This dressing can have two sides, an upper surface that will release molecules for re-epithelialization and provide a substrate for these cells. The bottom surface will promote regeneration of dermal tissue. This dressing is designed for dermal wound healing, including burns, full thickness dermal wounds and chronic or non-healing wounds and sores. Each fiber can have multi-component, multi-layer configuration to provide temporal release of drugs or factors that roughly correspond to the three phases of dermal wound healing.

As one example, in the case of a dressing designed for trauma patients, the first chemical to be released could be a pro-coagulant to help stop the bleeding. The next layer could then release cytokines to help recruit neutrophils and macrophages for the next phase of wound healing. Finally, a release of factors to help with reducing excessive scar tissue and to inhibit contractions, which are particularly disabling to burn patients.

3.5. Example 9

Fabrication of Artificial Arteries

It may be possible to construct an artificial artery using techniques described herein. A series of hollow, concentric cylindrical sections can be knitted, woven, braided or fabricated using non-woven technology with fibers loaded with various biological agents. The innermost cylinder is preferably tightly woven and contains drugs or agents to promote migrating, spreading and functioning of an intact endothelial cell layer. The next cylinder is composed of a woven or knitted architecture with fibers predominately circumferentially wound around the inner cylinder. This layer will induce the migration and proliferation of smooth muscle fibers, and promote the expression of elastin to create the internal elastic media. The next cylinder is composed of knitted or non-woven fibers and will contain drugs to promote the ingrowth of fibroblasts, macrophages and the creation of extracellular matrix. The last layer will compose longitudinal fibers that will promote the vascularization of the arterial cells via an artificial vasa vasorum, created by VEGF releasing fibers, or other promoters of angiogenesis.

3.6. Example 10

3.7. Drug Delivery Scaffold

In another application embodiment, these fibers can be used for drug delivery scaffolds in places where a fiber format is appropriate. For example, inside the eye, where microspheres or other formats may be more likely to interfere with the subject's vision, a fiber could be tacked down and not float into the field of view. Fibers may be able to stay in place better than microspheres or other formats such as nanoparticles, hydrogels, etc.

3.8. Example 11

3.9. Directed in Situ Angiogenesis

In this embodiment, one or more fibers containing one or more of the family of angiogenic factors such as VEGF, bFGF, angiotensin or others known to induce angiogenesis are placed into the body along the path where the directed angiogenesis is desired. As the fiber begins to release the angiogenic factors endothelial cells from the surrounding vasculature will be induced to migrate out towards the fiber(s) following a process similar to normal angiogenesis. The fiber(s) used may have one or more of the compositions described in this invention, or it may be a tube with VEGF or similar growth factor that is chemotactic for endothelial cells on the inside, and a different factor for smooth muscles on the outside. In this way, the size of the created vessel may be determined. In this application, cells are guided into initially cell-free scaffoldings by cell specific growth factors.

3.10. Example 12

3.11. Bone Fracture Healing

In another wound healing embodiment, proteins known to enhance bone fracture healing are loaded into a fiber. This fiber can then be wrapped around the bone at the site of the fracture, releasing the growth factors and enhancing the rate of fracture repair.

These fibers can either be in a helical structure (single or multiple helix), or they may be woven into a loose, open weave. Either in the helical or in the woven format, the fibers are placed around the bone fragments, holding them in place while releasing their growth factors.

In the case of a non-healing fracture that is due to lost or poor blood supply to the fracture site, a fiber or set of fibers containing VEGF or its equivalent may be used to enhance blood supply to the fractured area.

In this embodiment, bone fractures may be healed at accelerated rates compared to non-treated fractures, and non-unions may be healed in certain cases.

In yet a third bone healing application, fibers releasing pain relieving drugs may be used in the local area of the fracture. In this case, the fiber may be used in cases where plates, screws or other orthopedic devices are implanted or other surgical manipulations of the bone are performed. The local pain relief may lead the patient to apply load to the fracture sooner and may lead to a stronger and more rapid mend, as well as making life more comfortable for the patient.

3.12. Example 13

3.13. Skin Ulcer Healing

Similar to example 8 which described one form of dermal wound healing, another important example of this technology is the potential of healing chronic skin ulcers of various origins, such as diabetic foot ulcers, venous ulcers and general pressure sores. These conditions, and potentially other similar conditions may be healed based on creating a non-woven mesh of fibers that release factors known to accelerate dermal wound healing, for example, platelet derived growth factor (PDGF), transforming growth factor-beta (TGF-beta), and VEGF or similar protein. This non-woven mesh can be inserted or packed directly into the ulcer or wound, where these growth factors can help accelerate the wound-healing process. These dressings can be designed for healing dermal sores and ulcers. In this case, there is little need to reduce bleeding; rather one of the biggest needs of these patients, particularly those with diabetic ulcers is lack of blood supply to the wound site. Therefore, factors that induce angiogenesis may be able to increase circulation and help to rejuvenate the tissue at the site of the sore or ulcer.

Each dressing can be designed for the particular needs of the various types of wounds or sores by altering the biomolecules that are released, and the kinetics at which they are released.

3.14. Example 14

3.15. Muscle Grafts

In another embodiment, parallel arrays of fibers may be loaded with muscle stem cells. These stem cells can be of cardiac, smooth or skeletal muscle origin. Once these muscle stem cells are seeded onto the fiber array, the fibers can be mechanically stretched in vitro to help these cells align and differentiate properly. Alignment may also be achieved by using fibers of very small diameter. Our experience with axons indicates that with fibers on the order of 50 μm diameter tend to help cells align parallel to the axis of the fibers. Other fibers in this bundle can release angiogenic factors to create a vascular supply for the muscle cells. In the case of skeletal or smooth muscle tissue, fibers for nerve growth can also be included to induce the formation of neuromuscular junctions.

Various experimental conditions used to harvest, isolate, reproduce and differentiate these stem cells are known to those skilled in the art, and is not a part of this patent.

Example 15

Treatment of Glaucoma

Similar to drug delivery in the eye, described in example 10, and the neural stent described briefly in example 6, glaucoma may be treated by combining an intraocular drug delivery with a neural treatment applied to the optic nerve. Retinal ganglion cells undergo apoptosis leading to death of the axons of the optic nerve. It is hypothesized that if the cells could be supported both within the eye as well as along the path of the optic nerve, the cells may be able to survive. A fiber bundle that releases growth factors such as NT-4, BDNF, CNTF, may be applied topically to the exterior of the optic nerve. Simultaneously, fibers that release apoptosis inhibitors, or factors to support the retinal ganglion cells are implanted within the eye. This combined effort may prolong or save the sight of those suffering from glaucoma.

As is seen from the preceding examples, other tissues, organs, or structures are possible to weave once the basic physiologic structure is understood. This can be extended to organs of the digestive system, musculoskeletal system, urological system, circulatory system, and nervous system.

Example 16

Creation of a Gel or Hydrogel Core in a Biodegradable Polymer Sheath that Contains a Dispersed Aqueous Phase In another embodiment of the invention, gel bored fibers may also contain therapeutic agents in a dispersed aqueous, gel or hydrogel phase within the biodegradable polymer fiber wall. The apparatus and extrusion conditions are similar to example 1 except as noted here.

Once the polymer is dissolved in solvent (A), an aqueous solution or a gel or a hydrogel (including precursors) containing both the biomolecules(s) of interest and a surfactant is added to the polymer solution. Additionally, a surfactant can be added to solvent (A). The concentration of the aqueous phase is typically in the range of 1 to 70% v/v of the polymer solution, 4-20% being most typical for gel or hydrogel filled PLLA fibers. The surfactant can be one or a combination of substances familiar to those skilled in the art, such as bovine serum albumin (BSA), poly(vinyl alcohol), pluronics, or biological surfactants such as the family of phospholipids. Other surfactants not specifically mentioned here, but known to those skilled in the art are included by extension. In a typical use, BSA is used as the surfactant at concentrations ranging from about 10 fold to 100 fold higher than the biological molecule of interest, with typical concentrations ranging from 2 wt % to 50 wt % of the aqueous phase. Note that the inventors experience has demonstrated that high protein concentrations are difficult in the case of a gel or hydrogel, and therefore, the surfactant of choice may depend on the type of the dispersed phase.

Using some form of mechanical energy such as sonication, vortexing, or shear forces generated by forcing the liquid through a small orifice, a water-in-oil type emulsion is formed between the aqueous and organic phases. Depending on the volume of aqueous solution relative to the polymer solution, emulsification can be accomplished in stages, using partial additions of the aqueous phase until the total volume is incorporated into the polymer solution. This emulsion must be stable for periods far in excess of time required for extrusion to insure homogeneity of the emulsion throughout the extrusion process. The size of the dispersed aqueous phase droplets is primarily dependent on the quality of the surfactant, and the total amount of mechanical energy imparted to the system in forming the emulsion. The aqueous phase size is an important variable in both release kinetics and mechanical properties of the fiber. This emulsion is then used as the polymer solution, and all other details are the same as explained in example 1.

Example 17

Creation of a Gel or Hydrogel Exterior Fiber with a Biodegradable Polymer s Fiber Core Containing a Dispersed Aqueous, Gel, or Hydrogel Phase within the Fiber Wall This example is similar to example 2 in all details except that a dispersed phase is added to the polymer solution as described in example 16.

Example 18

Creation of a Gel or Hydrogel Exterior Hollow Fiber with a Dispersed Gel or Hydrogel Phase within the Fiber Wall This example is similar to example 3 in all details except that a dispersed phase is added to the polymer solution as described in example 16.

Example 19

Creation of a Water-Bore Fiber with a Dispersed Aqueous, Gel or Hydrogel Phase within the Wall of the Fiber This example is similar to example 4 in all details except that a dispersed phase is added to the polymer solution as described in example 16.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Aigner, Tegeler, Hutzler, Campoccia, Pavesio, Hammer, Kastenbauer, Naumann, "Cartilage tissue engineering with novel nonwoven structured biomaterial based on hyaluronic acid benzyl ester," *J. of Biomed. Materials Res.*, 42(2): 172-81, 1998.

Auerbach and Auerbach, "Angiogenesis inhibition: a review," *Pharmac. Ther.*, 63:265, 1994.

Breitbart, Grande, Kessler, Ryaby, Fitzsimmons, Grant, "Tissue engineered bone repair of calvarial defects using cultured periosteal cells," *Plastic & Reconstructive Surgery*, 101(3):567-74, 1998.

Cao, Rodriguez, Vacanti, Ibarra, Arevalo, Vacanti, "Comparative study of the use of poly(glycolic acid), calcium alginate and pluronics in the engineering of autologous porcine cartilage," *J. of Biomaterials Sci., Polymer Edition*, 9(5):475-87, 1998.

Dillon, Yu, Sridharan, Ranieri, Bellamkonda, "The influence of physical structure and charge on neurite extension in a 3D hydrogel scaffold," *J. of Biomaterials Sci., Polymer Ed.*, 9(10): 1049-69, 1998.

Elcin, Dixit, Lewin, Gitnick, "Xenotransplantation of fetal porcine hepatocytes in rats using a tissue engineering approach," *Artificial Organs*, 23(2): 146-52, 1999.

Fauza, Fishman, Mehegan, Atala, "Videofetoscopically assisted fetal tissue engineering: skin replacement," *J. of Pediatric Surgery*, 33(2):357-61, 1998.

Fidler and Ellis, "The implications of angiogenesis for the biology and therapy of cancer metastasis," *Cell*, 79:185, 1994.

Folkman and Klagsbrun, "Angiogenic factors," *Science*, 235: 442-447, 1987.

Folkman, "How is blood vessel growth regulated in normal and neoplastic tissue," *Cancer Res.*, 46:467, 1986.

Folkman, J., "Angiogenesis in cancer, vascular, rheumatoid and other disease," *Nature Med.*, 1:27, 1995.

Grande, Halberstadt, Naughton, Schwartz, Manji, "Evaluation of matrix scaffolds for tissue engineering of articular cartilage grafts," *J. of Biomed. Mat. Res.*, 34(2):211-20, 1997.

Gutsche, Lo, Zurlo, Yager, Leong, "Engineering of a sugar-derivatized porous network for hepatocyte culture," *Biomaterials*, 17(3):387-93, 1996.

Hoerstrup, Zund, Lachat, Schoeberlein, Uhlschmid, Vogt, Turina, "Tissue engineering: a new approach in cardiovascular surgery-seeding of human fibroblasts on resorbable mesh," *Swiss Surgery*, (Suppl.), 2:23-5, 1998.

Hoerstrup, Zund, Schoeberlein, Ye, Vogt, Turina, "Fluorescence activated cell sorting: a reliable method in tissue engineering of a bioprosthetic heart valve," *Annals of Thoracic Surgery*, 665(5):1653-7, 1998.

Isogai, Landis, Kim, Gerstenfeld, Upton, Vacanti, "Formation of phalanges and small joints by tissue-engineering," *J. of Bone & Joint Surgery, American Vol.*, 81(3):306-16, 1999.

Martin, Padera, Vunjak-Novakovic, Freed, "In vitro differentiation of chick embryo bone marrow stromal cells into cartilaginous and bone-like tissues," *J. of Orthopaedic Res.*, 16(2):181-9, 1998.

Nagy et al., "Pathogenesis of ascites tumor growth: vascular permeability factor, vascular hyperpermeability, and ascites fluid accumulation," *Cancer Res.*, 55:360, 1995.

Peppas and Langer, "New challenges in biomaterials," *Science*, 263:1715-1720, 1994.

Peter, Miller, Yasko, Yaszemski, Mikos, "Polymer concepts in tissue engineering," *J. of Biomed. Materials Res.*, 43(4): 422-7, 1998.

Sacks, Chuong, Petroll, Kwan, Halberstadt, "Collagen fiber architecture of a cultured dermal tissue," *J. of Biomed. Engineering*, 119(1):124-7, 1997.

Sambrook et al., *Molecular Cloning: A Laboratory Manual*, Cold Spring Harbor Laboratory Press, Cold Spring Harbor, N.Y., 1989.

Shinoka, Shum-Tim, Ma, Tanel, Isogai, Langer, Vacanti, Mayer, "Creation of viable pulmonary artery autografts through tissue engineering," *J. of Thoracic & Cardiovascular Surgery*, 115(3):536-45, 1998.

Sims, Butler, Cao, Casanova, Randolph, Black, Vacanti, Yaremchuk, "Tissue engineered neocartilage using plasma derived polymer substrates and chondrocytes," *Plastic & Reconstructive Surgery*, 101(6):1580-5, 1998.

Vunjak-Novakovic, Obradovic, Martin, Bursac, Langer, Freed, "Dynamic cell seeding of polymer scaffolds for cartilage tissue engineering," *Biotechnology Progress*, 14(2):193-202, 1998.

Whang, Tsai, Nam, Aitken, Sprague, Patel, Healy, "Ectopic bone formation via rhBMP-2 delivery from porous bioabsorbably polymer scaffolds," *J. of Biomed Materials Res.*, 42(4):491-9, 1998.

Wong and Mooney, "Synthesis and properties of biodegradable polymers used in tissue engineering," In: *Synthetic Biodegradable Polymer Scaffolds*, (Atala and Mooney, eds.), Birkhauser Press, Boston, Mass., pp. 51-82, 1997.

Yoo and Atala, "A novel gene delivery system using urothelial tissue engineered neoorgans," *J. of Urology*, 158(3 Pt 2):1066-70, 1997.

What is claimed is:

1. A method of manufacturing a fiber comprising,
   dissolving a biodegradable polymer in a first solvent to form a polymer solution, wherein said first solvent is poorly miscible in water;
   preparing a solution comprising a gel or hydrogel;
   promoting the internal gelation of the gel or hydrogel using a divalent cation;
   co-extruding the polymer solution and the solution comprising the gel or hydrogel into a coagulating bath, wherein the coagulating bath comprises a second solvent that is highly miscible with the first solvent; and
   forming at least one bicomponent fiber having a core-in sheath configuration, wherein the fiber comprises a first component and a second component, and wherein said first component is a biodegradable polymer and said second component comprises a gel or a hydrogel.

2. The method of claim 1 wherein the first component is located within the fiber sheath and the second component is located within the fiber core.

3. The method of claim 1 wherein the first component is located within the fiber core and the second component is located within the fiber sheath.

4. The method of claim 1 wherein the fiber sheath comprises the first component and the second component.

5. The method of claim 1 wherein the fiber core comprises the first component and the second component.

6. The method of claim 4 wherein the fiber core comprises gel or hydrogel.

7. The method of claim 4 wherein the fiber core comprises biodegradable polymer.

8. The method of claim 5 wherein the fiber sheath comprises gel or hydrogel.

9. The method of claim 5 wherein the fiber sheath comprises biodegradable polymer.

10. The method of claim 1 wherein the second component is randomly distributed across a cross section of the fiber.

11. The method of claim 1 wherein the second component is selectively distributed at specific locations across a cross section of the fiber.

* * * * *